United States Patent [19]

Van Lommen et al.

[11] Patent Number: 4,824,472

[45] Date of Patent: Apr. 25, 1989

[54] HERBICIDAL POLYCYCLYL SUBSTITUTED 1H-IMIDAZOLE-5-CARBOXYLIC ACIDS

[75] Inventors: Guy R. E. Van Lommen, Berlaar; Victor Sipido, Merksem; Wim G. Verschueren, Antwerpen, all of Belgium; William R. Lutz, Riehen, Switzerland

[73] Assignee: Janssen Pharmaceutica N.V., Beerse, Belgium

[21] Appl. No.: 137,384

[22] Filed: Dec. 23, 1987

[30] Foreign Application Priority Data

Dec. 31, 1986 [GB] United Kingdom ............... 8631091

[51] Int. Cl.$^4$ .................. A01N 43/50; C07D 233/90

[52] U.S. Cl. .......................................... 71/92; 71/90; 540/466; 540/476; 540/479; 540/543; 540/586; 540/593; 544/6; 544/55; 544/60; 544/70; 544/96; 544/126; 544/128; 544/139; 544/230; 544/361; 544/363; 544/364; 544/370; 546/16; 546/17; 546/79; 546/93; 546/106; 546/163; 546/209; 546/210; 548/131; 548/146; 548/147; 548/152; 548/160; 548/178; 548/179; 548/202; 548/216; 548/217; 548/235; 548/237; 548/238; 548/252; 548/253; 548/254; 548/269; 548/318; 548/321; 548/327; 548/336; 548/343

[58] Field of Search ............... 548/336, 337, 131, 146, 548/202, 235, 237, 238, 252, 253, 254, 269, 318, 321, 343, 147, 152, 160, 178, 179, 216; 544/55, 60, 96, 140, 6, 70, 126, 128, 139, 230, 361, 363, 364, 370; 546/209, 210, 211, 16, 17, 79, 93, 106, 163; 71/90; 540/466, 476, 479, 543, 586, 593

[56] References Cited

U.S. PATENT DOCUMENTS

3,485,917 12/1969 Godefroi ........................... 514/400
3,873,297  3/1975 Kupelian ............................. 71/78

FOREIGN PATENT DOCUMENTS

191514  8/1986 European Pat. Off. ............ 548/343
199206 10/1986 European Pat. Off. ............ 548/343

Primary Examiner—Richard A. Schwartz

[57] ABSTRACT

Novel herbicidal 1-cyclyl or polycyclyl substituted 1H-imidazole-5-carboxylic acid derivatives, compositions containing these compounds as active ingredients, and a method for controlling weeds, preferably selectively in crops of useful plants. Processes for making these novel compounds.

23 Claims, No Drawings

HERBICIDAL POLYCYCLYL SUBSTITUTED 1H-IMIDAZOLE-5-CARBOXYLIC ACIDS

BACKGROUND OF THE INVENTION

In U.S. Pat. No. 3,485,917 there are described a number of substituted 1H-imidazole-5-carboxylic acids as antifungals. Some of these compounds have been described as bud growth inhibitors in U.S. Pat. No. 3,873,297. EP-A-0,199,206 discloses cyclohexyl or hexenyl substituted imidazole-5-carboxylic acids having plant growth regulatory, herbicidal and fungicidal activity. In EP-A-0,191,514 a series of 1-substituted imidazole-5-carboximidates are taught to possess fungicidal properties.

DESCRIPTION OF THE INVENTION

The present invention in concerned with herbicidally active 1-cyclyl or polycyclyl substituted 1H-imidazole-5-carboxylic acids derivatives having the formula (I)

or a stereoisomeric form thereof, or a salt thereof, wherein $R^1$ is hydrogen or mercapto;
L is cyano, $COOR^{10}$, or a group of $-C(=G)-D-R^{13}$;
p is zero or the integer one to seven;
X is $CH_2$, O, $S(O)_n$ or $NR^{14}$, wherein n is 0, 1 or 2;
$R^2$, $R^3$, $R^4$, $R^5$, $R^6$, $R^7$, $R^8$ and $R^9$ are each independently hydrogen, $C_1-C_6$alkyl, mono- and di(aryl)$C_1-C_5$alkyl, hydroxy$C_1-C_5$alkyl, $C_1-C_5$alkyloxy$C_1-C_5$alkyl, $C_1-C_6$alkyloxy, halo, $C_3-C_7$alkenyl, trifluoromethyl, difluoromethoxy, or aryl; or two or four of the substituents $R^2$, $R^3$, $R^4$, $R^5$, $R^6$, $R^7$, $R^8$ or $R^9$ taken together may form one or two bivalent $C_1-C_5$alkanediyl, or $C_3-C_5$alkenediyl or $C_5-C_7$cycloalkanediyl radicals, said $C_1-C_5$alkanediyl, $C_3-C_5$alkenediyl or $C_5-C_7$ cycloalkanediyl being optionally substituted where possible with up to four radicals selected from the group consisting of $C_1-C_6$alkyl, mono- and di(aryl)$C_1-C_5$alkyl, hydroxy$C_1-C_5$alkyl, $C_1-C_5$alkyloxy$C_1-C_5$alkyl, $C_1-C_6$alkyloxy, halo, $C_3-C_7$alkenyl, trifluoromethyl, difluoromethoxy and aryl; or two or four of the substituents $R^2$, $R^3$, $R^4$, $R^5$, $R^6$, $R^7$, $R^8$ or $R^9$ being vicinally substituted may form one or more further bonds; and wherein one of the substituents on the said bivalent $C_1-C_5$alkanediyl, $C_3-C_5$alkenediyl or $C_5-C_7$cycloalkandiyl taken together with one of the substituents $R^2$, $R^3$, $R^4$, $R^5$, $R^6$, $R^7$, $R^8$ or $R^9$ may also form a bivalent $C_1-C_5$alkanediyl or $C_3-C_5$alkenediyl bridge which in turn may optionally be substituted where possible with up to four radicals selected from the group consisting of $C_1-C_6$alkyl, mono- and di(aryl)$C_1-C_5$alkyl, hydroxy$C_1-C_5$alkyl, $C_1-C_5$alkyloxy$C_1-C_5$alkyl, $C_1-C_6$alkyloxy, halo, $C_3-C_7$alkenyl, trifluoromethyl, difluoromethoxy and aryl; provided that the X-containing ring moiety being substituted on the 1-position of the imidazole ring is other than cyclohexyl or 1-cyclohexenyl being optionally substituted with one or more $C_1-C_6$alkyl, $C_1-C_6$alkyloxy, hydroxy$C_1-C_5$alkyl, $C_1-C_5$alkyloxy$C_1-C_5$alkyl or halo radicals;

$R^{10}$ is hydrogen, $C_1-C_7$alkyl being optionally substituted with one, two or three halo atoms, $C_3-C_7$alkenyl, $C_3-C_7$alkynyl, $C_3-C_7$cycloalkyl, $C_1-C_7$alkyloxy$C_1-C_7$alkyl, aryl$C_1-C_5$alkyl or a radical of formula $-N=C(R^{15})_2$;

E is oxygen, sulfur or $-NR-$;
R is hydrogen or $C_1-C_5$alkyl;
$R^{11}$ is hydrogen, $C_1-C_5$alkyl or trifluoromethyl;
$R^{12}$ is hydrogen, $C_1-C_5$alkyl, $C_1-C_5$alkyloxy, halo, trifluoromethyl, difluoromethoxy, cyano, nitro, amino, mono- and di$C_1-C_5$alkylamino or $C_1-C_5$-alkylcarbonylamino;
$R^{15}$ is hydrogen, $C_1-C_5$alkyl or two $R^{15}$ radicals may form a $C_4-C_6$alkanediyl radical;
G is $=N-R^{16}$, oxygen or sulfur;
D is sulfur, $-N(R^{17})-$, $-N(R^{18})-NH-$, $-N(R^{18})-O-$, $-\overset{|}{N}-C(=G)-OR^{18}$, $-\overset{|}{N}-C(=G)-R^{18}$, $-NSO_2-R^{18}$, $-\overset{|}{N}-CN$, $-NH-CH_2-CH_2-O-$ or $-\overset{|}{\underset{CH_2-CH_2-OH}{N}}-CH_2-CH_2-O-$;

$R^{13}$, $R^{17}$ and $R^{18}$ are independently selected from hydrogen, $C_1-C_5$alkyl, $C_3-C_5$alkenyl, $C_3-C_5$alkynyl, $C_3-C_7$cycloalkyl or $C_1-C_5$alkyl substituted with aryl, $C_3-C_7$cycloalkyl, $C_3-C_7$cycloalkyloxy, $C_1-C_5$alkyloxy, hydroxy, carboxyl or $C_1-C_5$alkyloxycarbonyl, whereas $R^{18}$ may also be aryl; or $R^{13}$ and $R^{17}$ together with the nitrogen atom to which they are attached may form a piperidinyl, pyrrolidinyl, 2-oxopiperidinyl, 2-oxopyrrolidinyl, morpholinyl, thiomorpholinyl, piperazinyl or 4-($C_1-C_5$alkyl)piperazinyl ring, each unsubstituted or substituted with one to three $C_1-C_5$alkyl groups;

$R^{14}$ is hydrogen, $C_1-C_5$alkyl, $C_1-C_5$alkanoyl, or 4-methylphenylsulfonyl; and $R^{16}$ is hydrogen or $C_1-C_5$alkyl;

aryl is phenyl optionally substituted with one to three substituents each independently selected from $C_1$–$C_5$alkyl, $C_1$–$C_5$alkyloxy and halo.

The radicals $R^2$, $R^3$, $R^4$, $R^5$, $R^6$, $R^7$, $R^8$ and $R^9$ as defined above may be substituted on any carbon atom making up the X-containing ring moiety, including the $CH_2$-groups of —$(CH_2)_p$— and X.

Surprisingly, the compounds of formula (I) exhibit strong herbicidal properties, and are therefore useful to control weeds. This property gains importance by the fact, that some crops of useful plants are not damaged, or are only slightly harmed when treated with compounds of formula (I) at high dosages. Consequently, the compounds of formula (I) are valuable selective herbicides in crops of useful plants, such as sugar beet, rape, soybeans, cotton, sunflower, cereals, especially wheat, barley, rye and oats, rice, both upland rice and paddy rice, and maize. Especially in rice crops a broad range of application rates can be employed, preferably if the rice crops are transplanted rice crops, and if the compounds of formula (I) are applied after transplantation. In maize crops selective herbicidal action is observed both at preemergence and at postemergence treatment. Additionally, some of the compounds of formula (I) show plant growth regulating properties.

The active ingredients (a.i.) of formula (I) are usually applied at application rates of 0.01 to 5.0 kg of active ingredient per hectare in order to achieve satisfying results. Sometimes, depending on the environmental conditions, the application rates may exceed the above designated limitations. However, the preferred application rates are between 0.05 kg and 1.0 kg a.i. per hectare.

As used in the foregoing definitions $C_1$–$C_5$alkyl denotes straight or branch chained saturated hydrocarbon radicals having from 1 to 5 carbon atoms, e.g. methyl, ethyl, propyl, methylethyl, the four butyl isomers and the pentyl isomers; $C_1$–$C_6$alkyl and $C_1$–$C_7$alkyl isomers and the pentyl isomers; $C_1$–$C_6$alkyl and $C_1$–$C_7$alkyl includes $C_1$–$C_5$alkyl radicals and the higher homologs thereof having respectively 6 and 7 carbon atoms; halo is fluoro, chloro, bromo or iodo, with fluoro and chloro being preferred; $C_3$–$C_5$alkenyl defines straight and branch chained hydrocarbon radicals containing one double bond and having from 3 to 5 carbon atoms such as, for example, 2-propenyl, 3-butenyl, 2-butenyl, 2-pentenyl, 3-pentenyl, 2-methyl-2-propenyl, or 3-methyl-2-butenyl, with 2-propenyl and 2-methyl-2-propenyl being preferred; $C_3$–$C_7$alkenyl includes $C_3$–$C_5$alkenyl and the hexenyl and heptenyl isomers; $C_3$–$C_5$alkynyl defines straight and branch chained hydrocarbon radicals containing one triple bond and having from 3 to 5 carbon atoms such as, for example, 2-propynyl, 2-butynyl, 3-butynyl, 2-pentynyl, 3-pentynyl or 4-pentynyl, with 2-propynyl being preferred; $C_3$–$C_7$alkynyl includes $C_3$–$C_5$alkynyl and the hexynyl and heptynyl isomers; and when said $C_3$–$C_7$alkynyl or said $C_3$–$C_7$alkenyl are substituted on a heteroatom, then the carbon atom of said $C_3$–$C_7$alkynyl or $C_3$–$C_7$alkenyl connected to said heteroatom preferably is saturated; $C_3$–$C_7$cycloalkyl defines cyclopropyl, cyclobutyl, cyclopentyl, cyclohexyl and cycloheptyl, with cyclopentyl and cyclohexyl being preferred; and $C_1$–$C_5$alkanoyl denotes formyl, acetyl, propionyl, butyryl, isobutyryl, valeryl, isovaleryl or pivaloyl; $C_3$–$C_6$alkanediyl, $C_4$–$C_6$alkenediyl and $C_1$–$C_5$alkanediyl define bivalent straight or branch chained saturated hydrocarbon radicals having from 3 to 6 or from 1 to 5 carbon atoms, e.g., methylene, 1,2-ethanediyl, 1,3-propanediyl, 1,4-butanediyl, 1,5-pentanediyl and 1,6-hexanediyl; $C_5$–$C_7$cycloalkendiyl denotes cyclopentanediyl, cyclohexanediyl and cycloheptanediyl; $C_3$–$C_5$alkenediyl defines bivalent straight and branch chained hydrocarbon radicals containing one double bond and having from 3 to 5 carbon atoms, e.g. propenediyl, butenediyl and pentenediyl, $C_1$–$C_7$alkyl being optionally substituted with one, two or three halo atoms defines haloalkyl radicals such as, for example, fluoromethyl, difluoromethyl, trifluoromethyl, chloromethyl, trichloromethyl, 2-fluoroethyl, 2,2,2-trifluoroethyl, 2,2,2-trichloroethyl and the like.

As typical examples of mono- and di-(aryl)$C_1$–$C_5$alkyl there may be mentioned phenylmethyl, phenylethyl, 4-chlorophenylmethyl, 4-chlorophenylethyl, 4-methoxyphenylmethyl, 3-methoxyphenylmethyl or diphenylmethyl, phenylmethyl being preferred.

The cyclic or polycyclic system attached to the imidazole ring encompasses the following typical structures which may be unsubstituted or substituted with the substituents $R^2$, $R^3$, $R^4$, $R^5$, $R^6$, $R^7$, $R^8$ and $R^9$, defined hereinabove:

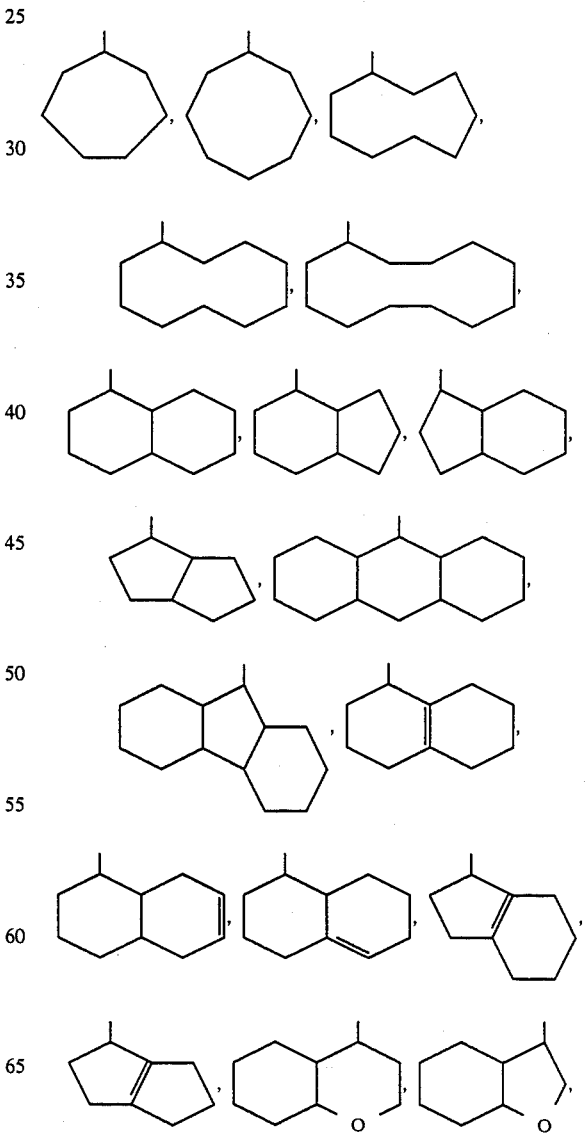

*-continued*

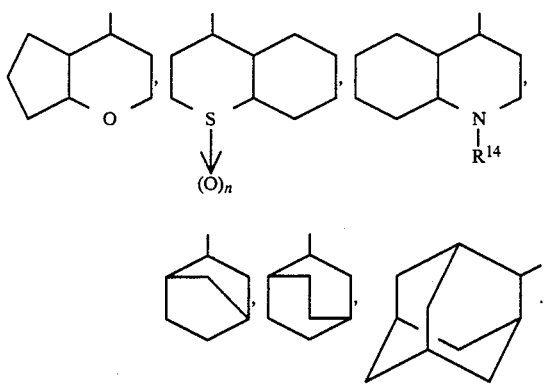

Depending on the nature of the moiety linked to the 1-position of the imidazole and/or the group L the compounds of formula (I) may contain asymmetrical carbon atoms. Unless otherwise mentioned or indicated, the chemical designation of compounds denotes the mixtures of all sterechemically isomeric forms. These mixtures contain all diastereomers and enantiomers of the basic molecular structure.

The absolute configuration of each chiral center may be indicated by the stereochemical descriptors R and S, this R and S notation corresponding to the rules described in Pure Appl. Chem. 1976, 45, 11–30. The relative configuration of the asymmetric centers in the compounds of formula (I) is denoted by cis and trans and where appropriate by the terms α and β, these stereochemical descriptors being used according to the rules described in Chemical Abstracts 1977 Index Guide, Appendix IV, § 203.

In some compounds the stereochemical configuration is not experimentally determined. In those cases it is conventionally agreed to designate the stereochemically isomeric form which is first isolated as "A", the second as "B", the third as "C", etc . . . without further reference to the actual stereochemical configuration.

Pure stereochemically isomeric forms of the compounds of formula (I) can be separated from the mixtures by art-known separation methods such as selective crystallization and chromatographic techniques, e.g., counter current distribution, column chromatography, high performance liquid chromatography and the like. Preferably, if a specific stereochemical form is desired, said compound will be synthesized by stereoselective methods of preparation. These methods will advantageously employ enantiomerically pure starting materials.

The invention also comprises the salts which the compounds of formula (I) are able to form with organic or inorganic bases such as amines, alkali metal bases and earth alkaline metal bases, or quaternary ammonium bases, or with organic or inorganic acids, such as mineral acids, sulfonic acids, carboxylic acids or phosphorus containing acids.

Examples of salt-forming mineral acids are hydrofluoric acid, hydrochloric acid, hydrobromic acid, hydroiodic acid, sulfuric acid, nitric acid, chloric acid, perchloric acid or phosphoric acid. Preferred salt-forming sulfonic acids are 4-methylbenzenesulfonic acid, benzenesulfonic acid, methanesulfonic acid or trifluoromethanesulfonic acid. Preferred salt-forming carboxylic acids are acetic acid, trifluoroacetic acid, benzoic acid, chloroacetic acid, phthalic acid, maleic acid, malonic acid and citric acid. Phosphorus containing acids are the various phosphonous acids, phosphonic acids and phosphinic acids.

Preferred salt-forming alkali metal hydroxides and earth alkaline metal hydroxides are the hydroxides of lithium, sodium, potassium, magnesium or calcium, most preferably those of sodium or potassium. Examples of suitable salt-forming amines are primary, secondary and tertiary aliphatic and aromatic amines such as methanamine, ethanamine, 1-priopanamine, 2-propanamine, the four butanamine isomers, N-methylmethanamine, N-ethylethanamine, 2-[(2-hydroxyethyl)amino]ethanol, N-propyl-1-propanamine, N-(1-methylethyl)-2-propanamine, N-butyl-1-butanamine, pyrrolidine, piperidine, morpholine, N,N-dimethylmethanamine, N,N-diethylethanamine, N,N-dipropyl-1-propanamine, quinuclidine, pyridine, quinoline and isoquinoline. Preferred amines are ethanamine, 1-propanamine, N-ethylethanamine or N,N-diethylethanamine, with 2-propanamine, 2-[(2-hydroxyethyl)amino]ethanol and 1,4-diazabicyclo[2.2.2]octane being most preferred. Examples of quaternary ammonium salts generally contain cations arising from ammonium hydroxides or ammonium halide salts, e.g. the tetramethylammonium, the trimethylphenylmethylammonium cation, the triethylphenylmethylammonium, and also the ammonium cation.

A particular subgroup amoung the compounds of formula (I) comprises those compounds of formula (I) wherein L is —COOR$^{10}$. Another particular subgroup comprises those compounds of formula (I) wherein L is CN or a radical —C(=G)—D—R$^{13}$.

A preferred subgroup of compounds are those compounds of formula (I) wherein the X-containing ring substituted at the 1-position of the imidazole ring is a radical of formula

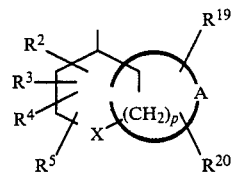

(a)

wherein A is $C_1$–$C_5$alkanediyl or $C_3$–$C_5$alkenediyl; X and R$^2$, R$^3$, R$^4$ and R$^5$ are as defined hereinabove and R$^{19}$ and R$^{20}$ independently have the same meaning of said R$^2$, R$^3$, R$^4$ and R$^5$.

Another preferred subgroup comprises those compounds of formula (I) wherein the 1-imidazole substituent is a radical of formula

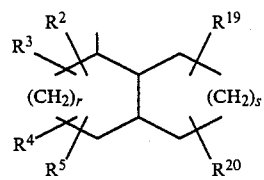

(b)

wherein r and s independently are one, two or three; and in the (CH$_2$)$_2$— containing ring one or two pairs of vicinal hydrogen atoms may be abstracted to form one or two extra bonds.

Particularly preferred compounds within the present invention are those preferred compounds of formula (I)

wherein L is —COOR$^{10}$; and/or —CN or a radical —C(=G)—D—R$^{13}$.

More particularly preferred compound within the present invention are those preferred or particularly preferred compounds wherein R$^{10}$ is hydrogen or C$_1$-C$_7$alkyl, G is O, D is NR$^{17}$, and R$^{13}$ and R$^{17}$ are hydrogen or C$_1$-C$_5$alkyl.

The most preferred compounds of the present invention are selected from methyl 1-(decahydro-1-naphthalenyl)-1H-imidazole-5-carboxylate, the salts and stereoisomeric forms thereof.

The preparation of the compounds of formula (I) is generally carried out by the following methods.

As used throughout the description of the synthesis procedures represented hereinafter, the symbol "—Y" defines a radical of formula

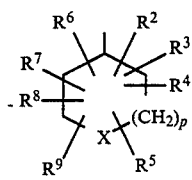

The compounds of formula (I) can be obtained by condensing a compound of formula

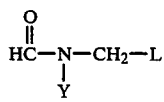

(II)

wherein L and Y are as defined hereinabove, with a C$_1$-C$_4$alkyl ester of formic acid in the presence of suitable base such as, for example, an alkali metal alkoxide or hydride, e.g. sodium methoxide, potassium ethoxide, sodium hydride, lithium hydride, and the like, in a reaction-inert solvent; and treating the resultant intermediate of formula

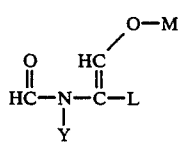

(III)

wherein L and Y are as defined hereinabove and M is an alkali metal atom, (a) with an alkali metal isothiocyanate in the presence of an acid, thus obtaining a 2-mercaptoimidazole of formula

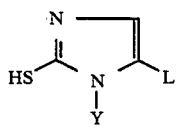

(I-a)

wherein Y and L are as defined hereinabove, which optionally is converted into a compound of formula

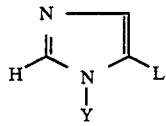

(I-b)

by reacting the starting compound with nitric acid optionally in the presence of an alkali metal nitrite, e.g. sodium nitrite; or with Raney-nickel in the presence of a lower aliphatic alcohol, preferably ethanol, at a temperature between 40° C. and 80° C.; or also by treating the starting compounds with an aqueous hydrogen peroxide solution preferably in the presence of a carboxylic acid, e.g. acetic acid; or (b) with a carboxylic acid amide of 1 to 3 carbon atoms, preferably formamide, in the presence of an acid at a temperature between 50° C. and 250° C., preferably between 120° C. and 170° C.; or (c) with an excess of ammonium carbonate or hydrogen carbonate in a suitable solvent, which may be a reaction-inert solvent or an acid, at a temperature between 20° C. and 200° C., preferably between 25° C. and the reflux temperature of the reaction mixture.

In the afore-mentioned processes reaction-inert solvents are, for example, aromatic hydrocarbons such as benzene, methylbenzene or dimethylbenzene; ethers such as, for example, 1,1'-oxybisethane, tetrahydrofuran or 1,4-dioxane; or other aprotic organic solvents. For the cyclization-reaction of the imidazole ring structure, strong mineral acids such as hydrohalic acids, e.g. hydrochloric acid, are most conveniently employed. In the ring-forming variant (c) other acids, e.g. acetic acid, can also be used. In this reaction an excess of acid of 5 to 50, preferably of 15 to 40 times the required molar amount is most preferably used. The excess of ammonium salt in this process is 2 to 50, preferably 10 to 30 times the required molar amount.

The compounds of formula (I-b) can also be prepared by the deamination reaction of a 4-amino-1H-imidazole derivative of formula (IV), wherein L and Y are as defined under formula (I) and L in particular is cyano or an amide group. Said deamination reaction involves a diazotation and a reductive dediazotation step which may be conducted sequentially, i.e. with isolation of the intermediate diazonium salt (IV-a) or in a one-pot fashion wherein said diazonium salt is reduced in situ.

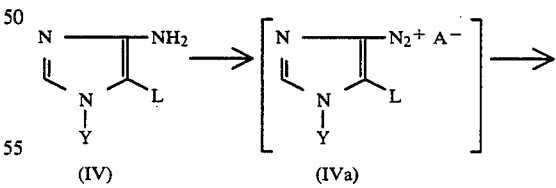

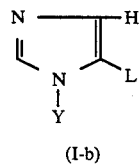

(I-b)

Treatment of the 4-amino-1H-imidazole derivative of formula (IV) in aqueous medium with an alkali metal nitrite, e.g. sodium or potassium nitrite, in the presence of an acid such as hydrochloric acid, sulfuric acid or nitric acid, or with nitronium tetrafluoroborate (NO+BF4−) yields the diazonium salt (IV-a). In the latter, L and Y are as defined hereinabove and A− represents an anion corresponding to the conjugated base of acid employed in the diazotation reaction or the tetrafluoroborate anion. The intermediate diazonium salts (IV-a) are reduced to the compounds of formula (I-b) by treatment with an appropriate reductant such as hypophosphic acid at an elevated temperature, preferably at the boiling temperature of the reaction mixture.

Alternatively, treatment of the 4-amino-1H-imidazole derivatives of formula (IV) with a $C_{1-5}$alkyl nitrite such as, 1,1-dimethylethyl nitrate or 3-methylbutyl nitrite in suitable aprotic solvent such as tetrahydrofuran, 1,4-dioxane, trichloromethane or N,N-dimethylformamide yields a compound of formula (I-b) directly. The latter deamination reaction may conveniently be conducted at an elevated temperature, generally at the boiling point of the reaction mixture.

The compounds of formula (I) can also be converted into each other following art-known functional group transformation reactions. The substituent L may be transformed into other substituents encompassed by the definition of L by convenient reactions known, in the art for the modification of carboxylic acid derivatives, e.g. by hydrolysis and esterification and/or transesterification and/or amidation or transamidation or conventional ring formation reactions.

The compounds of formula (I), wherein L is a radical of formula $-C(=G)-D-R^{13}$ or $-COOR^{10}$, can also be obtained from the structurally related carboxylic acids or thiocarboxylic acids or functional derivatives thereof by an amidation or esterification or from the related esters or amides by an appropriate transamidation or transesterification reaction. A preferred procedure is to convert the said acids into activated derivatives thereof following art-known procedures, for example, by treating the said acids with an appropriate halogenating agent, such as, for example, thionyl chloride, thionyl bromide, phosphoryl chloride, phosphoryl bromide, phosphorous trichloride, phosphorus tribromide, pentachlorophosphorane and the like. Or by dehydrating the carboxylic acid to the corresponding anhydride or by reacting the carboxylic acid with an acyl halide, e.g. acetyl or 2,2-dimethylpropanoyl chloride, ethyl or 1,1-dimethylethyl carbonochloridate and the like.

The thus obtained activated derivatives of formula (V)

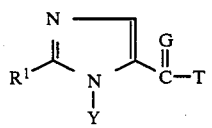

(V)

wherein $R^1$, G and Y are as defined hereinabove, and T is a reactive leaving group, e.g. halo, in particular chloro or bromo, an —O-acyl group, e.g. $-O-CO-C_1-C_5$alkyl or $-O-CO-O-C_1-C_5$alkyl and the like, or a group

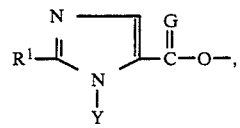

are reacted with the appropriate mercaptan or an amino compound of formula $H-D-R^{13}$, or with a hydroxy compound of formula $H-O-R^{10}$, wherein $R^{13}$, $R^{10}$ and D are as defined under formula (I). It may be appropriate to add a suitable base such as, for example, a trialkylamine, e.g. triethylamine to the reaction mixture in order to remove the acid which is liberated during the course of the reaction by salt-formation. Alternatively the compounds of formula (I) wherein L is a radical of formula $-C(=G)-D-R^{13}$ or $-COOR^{10}$ may also be prepared by treating the starting acids or thioacids and the amine, mercaptan or alcohol in the presence of a suitable reagent capable of forming amides, esters or thioesters, e.g. a carbodiimide such as dicyclohexylcarbodiimide (DCC), 2-halo-1-alkyl-pyridinium halides such as 2-chloro-1-methyl-pyridinium iodide, 1,1′-carbonylbis[1H-imidazole] and the like. The said amidation or esterification reactions are preferably conducted in a reaction-inert solvent such as, for example, a hydrocarbon, e.g. methylbenzene, dimethylbenzene; a halogenated hydrocarbon, e.g. dichloromethane, trichloromethane, an ether, e.g. tetrahydrofuran, dioxane; or a dipolar aprotic solvent, e.g. N,N-dimethylformamide, N,N-dimethylacetamide and the like solvents.

The cyano compounds (L is —CN) may be obtained by dehydration of the corresponding aminocarbonyl compounds. Suitable dehydrating agents for this procedure known in the art are, for example, pentachlorophosphorane, phosphoryl chloride, thionyl chloride, phosphorus pentoxide, anhydrides such as acetic acid anhydride, trifluoroacetic acid anhydride and the like agents. The reaction temperature depends mainly on the nature of the chosen dehydrating agent but in general it is contemplated that the process can conveniently be carried out at temperatures comprised between room temperature and the boiling point of the reaction mixture in particular between +20° C. and +120° C. If desired, said dehydration reaction can be run in inert organic solvents such as, for example, a halogenated hydrocarbon, e.g. dichloromethane, trichloromethane, an ether, e.g. tetrahydrofuran, dioxane; or a polar aprotic solvent, e.g. N,N-dimethylformamide, N,N-dimethylacetamide and the like solvents.

The tetrazoles can be obtained by reacting the corresponding nitriles (L is —CN) with an azide in a reaction-inert organic solvent such as N,N-dimethylformamide or dimethyl sulfoxide, at temperatures between +20° C. and +150° C.

The other heterocyclic compounds of formula (I), wherein L is

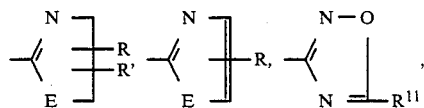

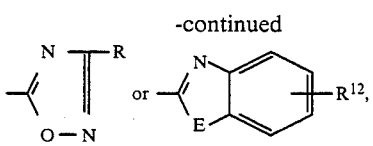 

are synthesized by treatment of the corresponding carboxylic acids (L is —COOH) or the derivatives thereof, for instance the acid chlorides, imino ethers, imino thioethers, amidines or amidoximes; with reagents such as diamines, aminoalcohols, aminomercaptans, amidoximes, α-haloketones, α-haloaldehydes, acid halogenides or carboxylic acid anhydrides. Reactions of this type are known in the art. For example general procedures are described in Chemistry of Carbon Compounds, Vol IV, Elsevier Publ. Co., 1957, in Heterocyclic Compounds, Wiley, N.Y., Vol. 5 (1957), Vol. 6 (1957), Vol. 7 (1961) and in the references cited therein.

The sulfur-containing compounds of formula (I) (L is —CS—D—$R^{13}$ can be produced by treating the correspondig oxygencontainig compounds of formula (L) (L is —CO—D—$R^{13}$) with phosphorus pentasulfide or with 2,4-bis(4-methoxyphenyl)-2,4-disulfide-1,3,2,4-dithiadiphosphetane (Lawesson's reagent). Preferentially, this reaction is carried out in the presence of a base and in an organic solvent such as N,N-dimethylformamide, N,N-dimethylacetamide, hexamethylphosphoric triamide, acetonitrile, methylbenzene or dimethylbenzene.

The amidoximes of formula (I) (L is —C($NH_2$)=N—O—R) can be obtained by reacting the nitriles (L is —CN) with hydroxylamine and optionally alkylating the resulting compound (L is —C($NH_2$)=N—OH) by treatment with an alkylating agent.

The amidines of formula (I) [L is —C(=NR)—NH—$R^{13}$] can be obtained by first converting a nitrile or nitrilium salt, prepared by treatment of the nitrile with $R_3O^+BF_4^-$, into an imino ether [L is —C(=N—R)—O—$C_1$—$C_5$ alkyl] by reaction with a $C_1$-$C_5$ alkanol in the presence of an acidic or basic catalyst and subsequently reacting the imino ether with an amine $R^{13}$—$NH_2$.

Y being —S— may be converted to the corresponding sulfoxide or sulfone by appropriate oxidation procedure, e.g. with a peroxide or a periodate.

If the synthesis of stereochemically pure isomers is intended, stereoselective reaction steps and conditions are recommended. On the other hand conventional methods of separation can be used for obtaining pure isomers from a mixture of stereochemical isomers.

The starting materials for the preparation of the novel compounds of formula (I) are known, or they can be obtained by known methods of synthesis.

For example the compounds of formula (II) can be obtained by reacting an aminomethylene derivative of formula.

Y—NH—$CH_2$—L   (VI)

wherein L and Y are as defined hereinabove with formic acid in the presence of acetic anhydride. In turn, the compounds of formula (VI) can be prepared by reacting an amine of formula (VII)

Y—$NH_2$   (VII)

wherein Y is as defined hereinabove, with a bromomethylene derivative of formula Br—$CH_2$—L   (VIII)

wherein L is as defined under formula (I), in the presence of an appropriate base, such as sodium carbonate.

The 4-amino-1H-imidazole derivatives of formula (IV) can be obtained by cyclizing an intermediate of formula

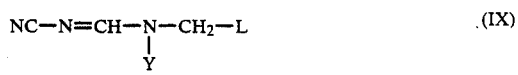

wherein Y and L are as defined hereinabove under catalysis of a base at elevated temperature in a suitable solvent, e.g. an alcohol. A preferred mode of carrying out said cyclization may comprise the reaction of the starting compound (IX) in an alcohol, in the presence of a catalytic amount of alkoxide obtained by dissolving an alkali metal in said alcohol, at the boiling point of the reaction mixture. Or, alternatively, by reacting (IX) with an alkali metal alkoxide in a polar solvent such as N,N-dimethylformamide or dimethyl sulfoxide. Generally, the reaction temperatures are in the range of +60° C. to +140° C.

The intermediates of formula (IX) in turn can be prepared by alkylating an amidine of formula

wherein Y is as defined hereinabove with a bromomethylene derivative of formula (VIII), in the presence of an appropriate base, such as, for example an alkali metal hydroxide, an alkali or earth alkaline metal carbonate or hydrogen carbonate, an earth alkaline oxide, an alkali metal alkoxide or a trialkylamine, e.g. sodium hydroxide, potassium hydroxide, sodium carbonate, potassium hydrogen carbonate, magnesium oxide, calcium oxide, sodium methoxide, sodium ethoxide, potassium ethoxide, potassium isopropoxide, pyridine, N,N-diethylethanamine and the like. In some instances, the addition of a crown-ether may be recommendable. The reaction may conveniently be conducted at temperatures between +10° C. and the boiling point of the reaction mixture, either without a solvent or in a solvent such as N,N-dimethylformamide, N,N-dimethylacetamide or dimethyl sulfoxide.

The compounds of formula (X) can be prepared by reacting an amine of formula (VII) with a $C_{1-5}$alkyl-N-cyanomethaimidate of formula

in an appropriate reaction-inert solvent such as trichloromethane, tetrahydrofuran, 1,4-dioxane, acetonitrile, N,N-dimethylformamide or N,N-dimethylacetamide. The said reaction can conveniently be carried out at temperatures between room temperature and the boiling point of the reaction mixture, in particular between +20° C. and +80° C. Removal of the $C_{1-5}$alkanol which is liberated during the course of the reaction and of the solvent by distillation under reduced pressure yields the N-cyanoamidine of formula (X) which in general need not be purified before further convertion.

The 4-amino-1H-imidazole derivatives of formula (IV) can alternatively be obtained from the amines of formula (VII), by a combined N-alkylating and cyclization reaction in a one-pot procedure. The latter procedure is conducted in the same solvents and bases as mentioned hereinabove for the two step synthesis.

The amines of formula (VII) are known compounds or can be obtained by the reduction of an oxime of formula $$Y^1=N-OH \qquad (XII),$$

wherein $Y^1$ is a geminal bivalent radical obtained by abstracting a further hydrogen atom from the carbon atom which links the Y-radical with the 1H-imidazole-5-carboxylic acid group. Said reduction is conveniently conducted with hydrogen in the presence of a noble metal catalyst or with a metallic hydride reagent, e.g. lithium tetrahydroaluminate or diborane in a suitable reaction-inert solvent such as an ether, e.g. tetrahydrofuran, 1,4-dioxane and the like. The oxime of formula (XII) may also be reduced electrochemically.

Said oxime (XII) in turn, can be prepared from the corresponding ketone of formula $$Y^1=O \qquad (XIII),$$

wherein $Y^1$ is as defined hereinabove, by. reacting said ketone of formula (XIII) with hydroxylamine.

The amines of formula (VII) can also be prepared by the reductive amination of a ketone of formula (XIII) with formamide in the presence of formic acid and subsequent removal of the N-formyl group by treatment with a hydrohalic acid, e.g. hydrochloric acid.

The intermediates of formula (VI) can also be obtained by the reductive N-alkylation reaction of a ketone of formula (XIII) with an aminomethylene derivative (XIV) wherein $Y^1$ and L are as defined hereinabove.

$$Y^1=O + H_2N-CH_2-L \xrightarrow{\text{reductive N-alkylation}}$$
(XIII)    (XIV)

$$Y-NH-CH_2-L$$
(VI)

Said reductive N-alkylation reaction may conveniently be carried out by hydrogenating a stirred and, if desired, heated mixture of reactants in a suitable reaction-inert organic solvent according to art-known catalytic hydrogenating procedures. Suitable solvents are, for example, alkanols, e.g. methanol, ethanol; ethers, such as tetrahydrofuran. The term "art-known catalytic hydrogenating procedures" means that the reaction is carried out under hydrogen atmosphere and in the presence of a catalyst such as, palladium-on-charcoal, platinum-on-charcoal and the like. In order to prevent the undesired further hydrogenation of certain functional groups in the reactants and the reaction products it may be advantageous to add an appropriate catalyst-poison to the reaction mixture, e.g. thiophene.

Alternatively, said reductive N-alkylation reactions may be conducted by treating a stirred and, if desired, heated mixture of the reactants with sodium cyanoborohydride, sodium borohydride, formic acid or a salt thereof, e.g. ammonium formiate.

Most of the ketones of formula (XIII) are known compounds or are conveniently prepared by known methods.

The compounds of formula (I) are stable compounds and no precautionary measures are required for handling them. When used at the indicated rates of application, the compounds of formula (I) have good selective herbicidal properties which make them most suitable for use in crops of useful plants, preferably in maize and in rice. In some cases damage is also caused to weeds which have only been controlled up to now with total herbicides.

At higher rates of application, all tested plants are so severely damaged in their development that they die.

The invention also relates to herbicidal compositions containing one or more inert carriers and, if desired, other adjuvants and as active ingredient a herbicidally effective amount of a compound of formula (I) as defined hereinabove. Further the invention relates to methods of controlling weeds, said method comprising the application to said weeds or to the locus thereof of a herbicidally effective amount of a compound of formula (I), a stereisomeric from or a salt thereof.

In the method of controlling weeds according to the invention the compounds of formula (I) are used in unmodified form or, preferably, together with the adjuvants conventionally employed in the art of formulation. They are therefore fomulated following art-known procedures to emulsifiable concentrates, directly sprayable or dilutable solutions, dilute emulsiions, wettable powders, soluble powders, dusts, granulates, and also encapsulations in e.g. polymer substances. As with the nature of the compositions, the methods of application, such as spraying, atomising, dusting, scattering or pouring, are chosen in accordance with the intended objectives and the prevailing circumstances.

The formulations, i.e. the compositions, preparations or mixtures containing the compound (active ingredient) of formula (I) and, where appropriate, a solid or liquid adjuvant, are prepared by known means, e.g. by homogeneously mixing and/or grinding the active ingredients with extenders, e.g. solvents, solid carriers and, where appropriate, surface-active compounds (surfactants).

Suitable solvents are aromatic hydrocarbons, preferably the fractions containing 8 to 12 carbon atoms, e.g. dimethylbenzene mixtures or substituted naphthalenes, phthalates such as dibutyl phthalate or dioctyl phthalate, aliphatic or alicyclic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethylsulfoxide or dimethylformamide, as well as vegetable oils or epoxidised vegetable oils such as epoxidised coconut oil or soybean oil; or water.

The solid carriers used e.g. for dusts and dispersible powders are normally natural mineral fillers such as calcite, talcium, kaolin, montmorillonite or attapulgite. In order to improve the physical properties it is also possible to add highly dispersed silicic acid or highly dispersed absorbent polymers. Suitable granulated absorbent carriers are of the porous type, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverised plant residues.

Depending on the nature of the compound of formula (I) to be formulated, suitable surface-active compounds are non-ionic, cationic and/or anionic surfactants having good emulsifying, dispersing and wetting porperties. The term "surfactants" will also be understood as comprising mixtures of surfactants.

Suitable anionic surfactants can be both water-soluble soaps and water-soluble synthetic surface-active compounds.

Suitable soaps are the alkali metal salts, earth alkaline metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. In addition, there may also be mentioned fatty acid methyltaurin salts.

More frequently, however, synthetic surfactants are used, especially fatty sulfonates, fatty sulfates, sulfonated benzimidazole derivatives or alkylarylsulfonates.

The fatty sulfonates or sulfates are usually in the form of alkali metal salts, earth alkaline metal salts or unsubstituted or substituted ammonium salts and contain an alkyl radical consisting of 8 to 22 carbon atoms, said alkyl also comprising radicals derived from acyl groups of fatty acids, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzene sulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide, or phospholipids.

Non-ionic surfactants are preferably polyglycol ether derivatives of aliphatic or cycloaliphatic alcohols, or saturated or unsaturated fatty acids and alkylphenols, said derivatives containing 3 to 10 glycol ether groups and 8 to 20 carbon atoms in the (alifatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionoic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Fatty acid esters of polyethylene sorbitan, such as polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methylsulfides or ethylsulfates, e.g. stearyltrimethylammonium chloride or benzyldi(2-chloroethyl)ethylammonium bromide.

The surfactants customarily employed in the art of formulation are described e.g. in the following publications:

"McCutcheon's Detergents and Emulsifiers Annual", MC Publishing Corp., Ridgewood, N.J., 1981; H. Stache, "Tensid-Taschenbuch", 2nd Edition, C. Hanser Verlag, Munich & Vienna, 1981, M. and J. Ash, "Encyclopedia of Surfactants", Vol. I–III, Chemical Publishing Co., New York, 1980-81.

The herbicidal compositions which are preferably employed in the method of the invention usually contain 0.1 to 95%, preferably 0.1 to 80%, of a compound of formula (I), 1 to 99.9%, of a solid or liquid adjuvant, and 0 to 25%, preferably 0.1 to 25%, of a surfactant.

Preferred compositions are composed in particular of the following constituents (%=percentage of weight):
Emulsifiable concentrates
  active ingredient: 1 to 20%, preferably 5 to 10%
  surfactant: 5 to 30%, preferably 10 to 20%
  liquid carrier: 50 to 94%, preferably 70 to 85%
Dusts
  active ingredient: 0.1 to 10%, preferably 0.1 to 1%
  solid carrier: 99.9 to 90%, preferably 99.9 to 99%
Suspension concentrates
  active ingredient: 5 to 75%, preferably 10 to 50%
  water: 94 to 25%, preferably 88 to 30%
  surfactant: 1 to 40%, preferably 2 to 30%
Wettable powders
  active ingredient: 0.5 to 90%, preferably 1 to 80%
  surfactant: 0.5 to 20%, preferably 1 to 15%
  solid carrier: 5 to 95%, preferably 15 to 90%
Granulates
  active ingredient: 0.5 to 30%, preferably 3 to 15%
  solid carrier: 99.5 to 70%, preferably 97 to 85%

The following examples are intended to illustrate and not to limit the scope of the present invention. Unless otherwise stated all parts therein are by weight.

EXPERIMENTAL PART

A. Preparation of Intermediates

EXAMPLE 1

(a) A mixture of 64 parts of octahydro-1(2H)-naphthalenone, 50 parts of methyl glycine hydrochloride, 2 parts of a solution of thiophene in methanol 4%, 560 parts of methanol and 50 parts of potassium acetate was hydrogenated at normal pressure and at room temperature with 5 parts of palladium-on-charcoal catalyst 10%. After the calculated amount of hydrogen was taken up, the catalyst was filtered off and the filtrate was evaporated. The residue was taken up in a mixture of water and trichloromethane. The whole was treated with a sodium hydroxide solution. The separated organic layer was dried, filtered and evaporated, yielding 82.2 parts (91.1%) of methyl N-(decahydro-1-naphthalenyl)glycine as a residue (intermediate 1).

(b) A mixture of 82.2 parts of methyl N-(decahydro-1-naphthalenyl)glycine, 36 parts of formic acid and 360 parts of methylbenzene was stirred for 4 hours at reflux temperature, using a water separator (another portion of 36 parts of formic acid was added each hour). After cooling, the separated organic layer was washed with a formic acid solution 20% and a sodium hydrogen carbonate solution, dried, filtered and evaporated, yielding 66 parts (71.3%) of methyl N-(decahydro-1-naphthalenyl)-N-formylglycine as a residue (intermediate 2).

In a similar manner there were also prepared:

methyl N-formyl-N-(octahydro-1H-inden-1-yl)glycine as a residue (intermediate 3); and methyl N-formyl-N-(octahydro-4H-1-benzopyran-4-yl)glycine as a residue (intermediate 4).

EXAMPLE 2

(a) To a stirred solution of 203 parts of decahydro-1-naphthalenamine and 161 parts of N,N-diethylethanamine in 40 parts of hexane were added dropwise 122 parts of methyl bromoacetate. Upon complete addition, stirring was continued for 24 hours at room temperature. The precipitate was filtered off and the filtrate was concentrated to dry, yielding methyl N-(decahydro-1-naphthalenyl)glycine (intermediate 5).

(b) 150 Parts of methyl N-(decahydro-1-naphthalenyl)glycine were added dropwise to 372 parts of formic acid while cooling (5° C.). Upon complete addition, 110 parts of acetic acid anhydride were added. The reaction mixture was stirred for 17 hours at room temperature. The whole was distilled in vacuo, yielding 142.8 parts (89.4%) of methyl N-(decahydro-1-naphthalenyl)-N-formylglycine as a residue (intermediate 6).

EXAMPLE 3

(a) To a stirred and heated (<40° C.) solution of 96 parts of decahydro-2,2-dimethyl-1-naphthalenamine in 400 parts of ethanol were added dropwise 48 parts of ethyl N-cyanomethanimidate. Upon complete addition, stirring was continued for 2 hours. The precipitated product was filtered off (and set aside) and the filtrate was evaporated. The residue was treated with 2,2'-oxybispropane. The precipitated product was filtered off and combined with the product, which was set aside (see above). Both were crystallized from acetonitrile. The product was filtered off and dried, yielding 67 parts (54.1%) of N'-cyano-N-(decahydro-2,2-dimethyl-1-naphthalenyl)methanimidamide; mp. 227.6° C. (intermediate 7).

(b) To a stirred solution of 67 parts of N'-cyano-N-(decahydro-2,2-dimethyl-1-naphthalenyl)methanimidamide in 550 parts of dimethyl sulfoxide were added 34 parts of 2-methyl-2-propanol, potassium salt. After stirring for 1 hour at room temperature, 46 parts of methyl 2-bromoacetate were added dropwise to the thus obtained mixture. Upon complete addition, stirring was continued for 2 hours at room temperature. The reaction mixture was poured into water and the product was extracted with ethyl acetate. The extract was dried, filtered and evaporated. The residue was taken up in methanol and treated with 17 parts of sodium methoxide. After stirring for 4 hours at room temperature, the mixture was evaporated. The residue was taken up in trichloromethane. The organic layer was washed with water, dried, filtered and evaporated. The residue was purified by column chromatography (HPLC) over silica gel using a mixture of hexane and ethyl acetate (80:20 by volume) as eluent. The pure fractions were collected and the eluent was evaporated, yielding 4.5 parts (4.9%) of (±)-methyl [1α,4aβ,8aβ]-4-amino-1-decahydro-2,2-dimethyl-1-naphthalenyl)-1H-imidazole-5-carboxylate; mp. 209.9° C. (intermediate 8).

B. Preparation of the final compounds

EXAMPLE 4

To a stirred solution of methyl N-(decahydro-1-naphthalenyl)-N-formylglycine in 900 parts of tetrahydrofuran and 127 parts of methyl formate were added suitable amounts of sodium hydride. After stirring for 18 hours at room temperature, 350 parts of deionised water and 1.4 parts of 1,1'-oxybisethane were added to the mixture. The separated aqueous layer was acidified with 132.7 parts of concentrated hydrochloric acid and 280 parts of methanol were added. The whole was heated to 40°–50° C. and treated with a solution of 92.7 parts of potassium thiocyanate in 200 parts of deionised water. The whole was stirred for 22 hours at room temperature. The precipitated product was filtered off and crystallized from methanol. The product was filtered off and dried, yielding methyl 2-mercapto-N-(decahydro-1-naphthalenyl)-1H-imidazole-5-carboxylate; mp. 179°–181° C. (compound 1.15).

EXAMPLE 5

82.4 Parts of methyl N-(decahydro-1-naphthalenyl)-2-mercapto-1H-imidazole-5-carboxylate were added portionwise to a solution of 5.8 parts of sodium nitrite and 52.4 parts of nitric acid in 500 parts of deionised water at 40°–50° C. The precipitate was filtered off and treated with an aqueous sodium carbonate solution 10%. The product was extracted with trichloromethane. The extract was dried, filtered and evaporated, converted into the nitrate salt in 2-propanone and 2,2'-oxybispropane. The salt was filtered off and dried, yielding 39 parts (53.1%) of methyl N-(decahydro-1-naphthalenyl)-2-mercapto-1H-imidazole-5-carboxylate; mp. 84°–86° C. (compound 1.16).

EXAMPLE 6

A mixture of 66.0 parts of methyl N-(decahydro-1-naphthalenyl)-N-formylglycine, 12.52 parts of a sodium hydride dispersion 50%, 360 parts of tetrahydrofuran and 45 parts of methyl formate was stirred overnight at room temperature. The reaction mixture was evaporated and the residue was taken up in water and trichloromethane. The whole was acidified with concentrated hydrochloric acid. The separated, organic layer was dried, filtered over diatomaceous earth and evaporated. The residue was taken up in 72 parts of concentrated hydrochloric acid, 480 parts of methanol, 50.4 parts of potassium thiocyanate and 250 parts of water. The whole was stirred overnight at 60° C. After cooling, 1000 parts of water were added. The product was extracted with dichloromethane. The extract was dried, filtered and evaporated, yielding 77 parts (100%) of methyl 1-(decahydro-1-naphthalenyl)-2-mercapto-1H-imidazole-5-carboxylate as a solid residue (compound 1.01).

EXAMPLE 7

A mixture of 77.7 parts of methyl 1-(decahydro-1-naphthalenyl)-2-mercapto-1H-imidazole-5-carboxylate, 157 parts of nitric acid, 300 parts of water and 0.2 parts of sodium nitrite was stirred for 1.5 hours at room temperature. The reaction mixture was poured into crushed ice and treated with a sodium hydroxide solution. The product was extracted with dichloromethane. The extract was dried, filtered and evaporated. The residue was converted into the nitrate salt in 1,1'-oxybisethane. The salt was filtered off and dried, yielding 33.9 parts (39.4%) of methyl 1-(decahydro-1-napthalenyl)-1H- imidazole-5-carboxylate mononitrate; mp. 148.6° C. (compound 1.03).

EXAMPLE 8

17.9 Parts of methyl 1-(decahydro-1-naphthalenyl)-1H-imidazole-5-carboxylate mononitrate (compound 1.03) were purified by column chromatography over silica gel using a mixture of dichloromethane and methanol (99:1 by volume) as eluent. The first fraction was collected and the eluent was evaporated (the following fraction was set aside). The residue was converted into the nitrate salt in 21 parts of 1,1'-oxybisethane. The salt was filtered off and dried, yielding 2.0 parts (11.1%) of methyl ($\pm$)-[1$\alpha$,4a$\alpha$,8a$\beta$]-1-(decahydro-1-naphthalenyl)-1H-imidazole-5-carboxylate mononitrate; mp. 167.8° C. (compound 1.08). The fraction, which was set aside, was evaporated. The residue was purified by column chromatography over silica gel using a mixture of hexane and ethyl acetate (70:30 by volume) as eluent. The second fraction was collected and the eluent was evaporated. The residue was converted into the nitrate salt in 1,1'-oxybissethane. The salt was filtered off and dried, yielding 1.9 parts (10.6%) of methyl ($\pm$)-[1$\beta$,4a$\alpha$,8a$\beta$]-1-(decahydro-1-naphthalenyl)-1H-imidazole-5-carboxylate mononitrate; mp. 170.6° C. (compound 1.12). The third fraction was collected and the eluent was evaporated. The residue was converted into the nitrate salt in 1,1'-oxybisethane. The salt was filtered off and dried, yielding 0.44 parts (2.4%) of methyl 1-(decahydro-1-naphthalenyl)-1H-imidazole-5-carboxylate mononitrate (mixture of two 4a,8a-cis-isomers); mp. 192.2° C. (compound 1.18).

EXAMPLE 9

A mixture of 6.0 parts of methyl ($\pm$)-[1$\alpha$,4a$\alpha$,8a$\beta$]-1-(decahydro-1-naphthalenyl)-1H-imidazole-5-carboxylate, 6 parts of a sodium hydroxide solution 50% and 100 parts of water was stirred for 2 hours at reflux temperature. The reaction mixture was acidified with an acetic acid solution and the product was extracted with trichloromethane. The extract was dried, filtered and evaporated. The residue was boiled for 2 hours in acetonitrile. The precipitated product was filtered off and dried, yielding 4.3 parts (75.2%) of ($\pm$)-[1$\alpha$,4a$\alpha$,8a$\beta$]-1-(decahydro-1-naphthalenyl)-1H-imidazole-5-carboxylic acid; mp. 217.20° C. (compound 1.09).

EXAMPLE 10

To a stirred and heated (60° C.) mixture of 2.8 parts of ($\pm$)-[1$\alpha$,4a$\alpha$,8a$\beta$]-1-(decahydro-1-naphthalenyl)-1H-imidazole-5-carboxylic acid and 135 parts of N,N-dimethylformamide were added 1.83 parts of 1,1'-carbonyl-bis[1H-imidazole]. After stirring for 1 hour at 20° C., 3.0 parts of methanamine were added and stirring was continued overnight. The reaction mixture was evaporated and the residue was taken up in water and trichloromethane. The separated organic layer was washed twice with water, dried, filtered and evaporated. The residue was dried in vacuo at 60° C., yielding 1.8 parts (60.9%) of ($\pm$)-[1$\alpha$,4a$\alpha$,8a$\beta$]-1-(decahydro-1-naphthalenyl)-N-methyl-1H-imidazole-5-carboxamide; mp. 156.9° C. (compound 1.10).

EXAMPLE 11

A mixture of 8.0 parts of ($\pm$)-[1$\alpha$,4a$\alpha$,8a$\beta$]-1-(decahydro-1-naphthalenyl)-1H-imidazole-5-carboxylic acid, 5.25 parts of 1,1'-carbonyl-bis[1H-imidazole] and 90 parts of tetrahydrofuran was stirred for 1 hour at room temperature. Gaseous ammonia was bubbled through the mixture during 2 hours. After stirring over weekend at room temperature, the reaction mixture was evaporated. The residue was taken up in water and dichloromethane. The precipitated product was filtered off and crystallized from acetonitrile. The product was filtered off and dried, yielding 3.1 parts (39.1%) of ($\pm$)-[1$\alpha$,4a$\alpha$,8a$\beta$]-1-decahydro-1-naphthalenyl)-1H-imidazole-5-carboxamide; mp. 207.7° C. (compound 1.50).

EXAMPLE 12

To a stirred and cooled (5° C.) mixture of 9.0 part of ($\pm$)-[1$\alpha$,4a$\alpha$,8a]-1-(decahydro-1-naphthalenyl)-1H-imidazole-5-carboxamide, 6.3 parts of pyridine and 125 parts of 1,4-dioxane were added dropwise 9.45 parts of trifluoroacetic acid anhydride during 15 minutes. Upon complete addition, stirring was continued first for 1 hour at 5° C. and then overnight at 20° C. The reaction mixture was evaporated and the residue was taken up in water. The product was extracted with dichloromethane. The extract was washed with a diluted sodium hydroxide solution, dried, filtered and evaporated. The residue was taken up in 2,2'-oxybispropane (+ activated charcoal) and filtered over diatomaceous earth. The filtrate was evaporated and the residue was converted into the hydrochloride salt in 2,2'-oxybispropane and 2-propanol. The salt was filtered off and dried, yielding 2.3 parts (24.0%) of ($\pm$)-[1$\alpha$,4a$\alpha$,8a$\beta$]-1-(decahydro-1-naphthalenyl)-1H-imidazole-5-carbonitrile minohydrochloride; mp. 203.4° C. (compound 1.65).

EXAMPLE 13

To a stirred and heated (60° C.) solution of 1.1 parts of 2-methyl-2-propylnitrite in 9.4 parts of N,N-dimethylformaide was added a solution of 2.2 parts of ($\pm$)-methyl [1$\alpha$,4a$\beta$,8a$\beta$]-4-amino-1-(decahydro-2,2-dimethyl-1-naphthalenyl)-1H-imidazole-5-carboxylate in 47 parts of C. After stirring for 15 minutes at 60° C., the reaction mixture was poured into water and the product was extracted with 1,1'-oxybisethane. The extract was washed three times with water, dried, filtered and evaporated. The residue was converted into the nitrate salt in 14 parts of 2,2'-oxybispropane. The salt was filtered off and dried, yielding 1 part (40.4%) of ($\pm$)-methyl [1$\alpha$,4a$\beta$,8a$\beta$]-1-(decahydro-2,2-dimethyl-1-naphthalenyl)-1H-imidazole-5-carboxylate mononitrate; mp. 151.7° C. (compound 1.66).

EXAMPLE 14

(a) A mixture of 22.4 parts of methyl N-formyl-N-(octahydro-1H-inden-1-yl)glycine, 4.5 parts of a sodium hydride dispersion 50%, 270 parts of tetrahydrofuran and 30 parts of methyl formate was stirred for 3 hours at room temperature. The reaction mixture was evaporated and the residue was taken up in water and 1,1'-oxybisethane. The separated aqueous layer was acidified with concentrated hydrochloric acid. The product was extracted with 1,1'-oxybisethane. The combined organic layers were evaporated. The residue was taken up in 36 parts of concentrated hydrochloric acid, 280 parts of methanol, 15.0 parts of potassium thiocyanate and 200 parts of water. The whole was stirred first overnight at 60° C. and then over weekend at room temperature. The precipitated product was filtered off (the filtrate was set aside) and dried, yielding a first fraction of 1.0 part (3.7%) of methyl 2-mercapto-1-(octahydro-1H-inden-1-yl)-1H-imidazole-5-carboxylate.

The filtrate, which was set aside (see above) was evaporated. The residue was taken up in a mixture of water and trichloromethane. The separated organic layer was dried, filtered and evaporated, yielding a second fraction of 7.0 parts (26.5%) of methyl 2-mercapto-1-(octahydro-1e,uns/H/ -inden-1-yl)-1H-imidazole-5-carboxylate. Total yield: 8.0 parts (30.2%) of methyl 2-mercapto-1-(octahydro-1H-inden-1-yl)-1H-imidazole-5-carboxylate; mp. 144.9° C. (compound 2.01).

A mixture of 38.8 parts of methyl 2-mercapto-1-(octahydro-1H-inden-1-yl)-1H-imidazole-5-carboxylate, 0.1 parts of sodium nitrite, 75 parts of nitric acid and 100 parts of water was stirred for 1 hour at room temperature. The reaction mixture was taken up in crushed ice and treated with sodium hydroxide solution. The product was extracted with dichloromethane. The extract was dried, filtered and evaporated. The residue was purified by column chromatography (HPLC) over silica gel using a mixture of methanol, water and ammonium acetate (66:33:1 by volume) as eluent.

The third fraction was collected and the eluent was evaporated. The residue was converted into the hydrochloride salt in 1,1'-oxybisethane. The salt was filtered off and dried, yielding 1.5 parts (3.8%) of methyl (C)-1-(octahydro-1H-inden-1-yl)-1H-imidazole-5-carboxylate monohydrochloride; mp. 153.5° C. (compound 2.03). The second fraction was collected and the eluent was evaporated. The residue was converted into the hydrochloride salt in 1,1'-oxybisethane. The salt was filtered off and dried, yielding 8.3 parts (21.1%) of methyl (A+B+C)-1-octahydro-1H-inden-1-yl)-1H-imidazole-5-carboxylate monohydrochloride; mp. 146.6° C. (compound 2.02).

EXAMPLE 15

(a) 7.0 Parts of a sodium hydride dispersion 50% were added portionwise to a solution of 36 parts of methyl N-formyl-N-(octahydro-4H-1-benzopyran-4-yl)glycine in 211 parts of tetrahydrofuran. Upon complete addition, stirring was continued overnight at 60° C. The reaction mixture was evaporated and the residue was taken up in water. The whole was extracted with 1,1'-oxybisethane. The aqueous layer was acidified with concentrated hydrochloric acid and the product was extracted with dichloromethane. The extract was dried, filtered and evaporated. The residue was combined with 96 parts of methanol, 36 parts of concentrated hydrochloric acid, a solution of 18.7 parts of potassium thiocyanate in 35 parts of water and 110 parts of water. The whole was stirred overnight at 60° C. The precipitated product was filtered off (the filtrate was set aside) and dried in vacuo at 80° C., yielding a first fraction of 14.5 parts (34.9%) of methyl 1-(octahydro-4H-1-benzopyran-4-yl)-2-mercapto-1H-imidazole-5-carboxylate.

The filtrate, which was set aside (see above) was extracted with dichloromethane. The extract was washed with water, dried, filtered and evaporated, yielding a second fraction of 11 parts (26.5%) of methyl 1-(octahydro-4H-1-benzopyran-4-yl)-2-mercapto-1H-imidazole-5-carboxylate.

Total yield: 25.5 parts (61.4%) of methyl 1-(octahydro-4H-1-benzopyran-4-yl)-2-mercapto-1H-imidazole-5-carboxylate (compound 6.01).

(b) A mixture of 25 parts of methyl 1-(octahydro-4H-1-benzopyran-4-yl)-2-mercapto-1H-imidazole-5-carboxylate, 37.5 parts of concentrated nitric acid and 80 parts of water was stirred for 2 hours at room temperature. The reaction mixture was diluted with water and the whole was treated with a sodium hydroxide solution while cooling in an ice bath. The product was extracted with dichloromethane. The extract was dried, filtered and evaporated. The residue was purified by column chromatography (HPLC) over silica gel using a mixture of trichloromethane, petroleum ether and methanol (50:48:2 by volume) as eluent.

The first fraction was collected and the eluent was evaporated. The residue was converted into the nitrate salt in a mixture of 2-propanone and 1,1'-oxybisethane. The salt was filtered off and dried in vacuo at 60° C., yielding 1.6 parts (5.8%) of methyl (±)-[4α,8aα,4aβ]-1-(octahydro-4H-1-benzopyran-4-yl)-1H-imidazole-5-carboxylate mononitrate; mp. 158.7° C. (compound 6.02).

The second fraction was collected and the eluent was evaporated. The residue was converted into the nitrite salt in a mixture of 2-propanone and 1,1'-oxybisthane. The salt was filtered off and dried in vacuo at 60° C., yielding 2.1 parts (7.6%) of methyl (±)-[4β,8aα,4aβ]-1-(octahydro-4H-1-benzopyran-4-yl)-1H-imidazole-5-carboxylate mononitrate; mp. 172.7° C. (compound 6.03).

All other compounds listed in tables 1 to 13 can be obtained by analogous methods of preparation.

TABLE 1

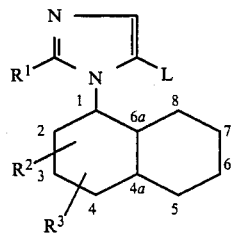

| Comp. No. | $R^1$ | L | $R^2$ | $R^3$ | stereochemistry | physical data |
|---|---|---|---|---|---|---|
| 1.01 | SH | COOCH$_3$ | H | H | | solid residue (A + B + C + D) |
| 1.02 | H | COOCH$_3$ | H | H | | |
| 1.03 | H | COOCH$_3$ | H | H | | .HNO$_3$/mp.148.6° C. (A + B + C + D) |
| 1.04 | H | COOH | H | H | | mp. 208.1° C. (A + B + C + D) |
| 1.05 | H | CO—NH—CH$_3$ | H | H | | mp. 142.6° C. (A + B + C + D) |
| 1.06 | SH | COOCH$_3$ | H | H | (±)-[1α,4aα,8aα] | |
| 1.07 | H | COOCH$_3$ | H | H | (±)-[1α,4aα,8aβ] | |
| 1.08 | H | COOCH$_3$ | H | H | (±)-[1α,4aα,8aβ] | .HNO$_3$/mp. 167.8° C. |
| 1.09 | H | COOH | H | H | (±)-[1α,4aα,8aβ] | mp. 217.2° C. |
| 1.10 | H | CO—NH—CH$_3$ | H | H | (±)-[1α,4aα,8aβ] | mp. 156.9° C. |

TABLE 1-continued

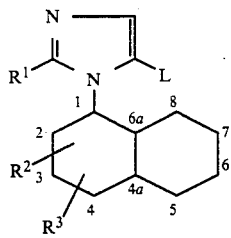

| Comp. No. | R¹ | L | R² | R³ | stereochemistry | physical data |
|---|---|---|---|---|---|---|
| 1.11 | SH | COOCH₃ | H | H | (±)-[1β,4aα,8aβ] | |
| 1.12 | H | COOCH₃ | H | H | (±)-[1β,4aα,8aβ] | .HNO₃/mp. 170.6° C. |
| 1.13 | H | COOH | H | H | (±)-[1β,4aα,8aβ] | |
| 1.14 | H | CO—NH—CH₃ | H | H | (±)-[1β,4aα,8aβ] | |
| 1.15 | SH | COOCH₃ | H | H | 4a,8a-cis | mp. 179–181° C. |
| 1.16 | H | COOCH₃ | H | H | 4a,8a-cis | mp. 84–86° C. |
| 1.17 | H | COOCH₃ | H | H | 4a,8a-cis | .HNO₃/mp. 176.5° C. |
| 1.18 | H | COOCH₃ | H | H | 4a,8a-cis | (C + D)/.HNO₃/mp. 192.2° C. |
| 1.19 | SH | COOCH₃ | 2CH₃ | H | | |
| 1.20 | H | COOCH₃ | 2CH₃ | H | | |
| 1.21 | H | COOH | 2CH₃ | H | | |
| 1.22 | H | CO—NH—CH₃ | 2CH₃ | H | | |
| 1.23 | SH | COOCH₃ | 2CH₃ | 2CH₃ | | |
| 1.24 | H | COOCH₃ | 2CH₃ | 2CH₃ | | |
| 1.25 | H | CO—OH | 2CH₃ | 2CH₃ | (±)-[1α,4aα,8aβ] | |
| 1.26 | H | CO—NH—CH₃ | 2CH₃ | 2CH₃ | (±)-[1α,4aα,8aβ] | |
| 1.27 | SH | CO—O—C₂H₅ | H | H | (±)-[1α,4aα,8aβ] | |
| 1.28 | H | CO—O—C₂H₅ | H | H | (±)-[1α,4aα,8aβ] | |
| 1.29 | SH | CO—O—C₃H₇—n | H | H | (±)-[1α,4aα,8aβ] | |
| 1.30 | H | CO—O—C₃H₇—n | H | H | (±)-[1α,4aα,8aβ] | |
| 1.31 | SH | CO—O—C₄H₉—n | H | H | (±)-[1α,4aα,8aβ] | |
| 1.32 | H | CO—O—C₄H₉—n | H | H | (±)-[1α,4aα,8aβ] | |
| 1.33 | SH | CO—O—cyclohexyl | H | H | (±)-[1α,4aα,8aβ] | |
| 1.34 | H | CO—O—cyclohexyl | H | H | (±)-[1α,4aα,8aβ] | |
| 1.35 | SH | CO—O—CH₂—CH=CH₂ | H | H | (±)-[1α,4aα8aβ] | |
| 1.36 | H | CO—O—CH₂—CH=CH₂ | H | H | (±)-[1α,4aα,8aβ] | |
| 1.37 | SH | CO—O—CH₂—C≡CH | H | H | (±)-[1α,4aα,8aβ] | |
| 1.38 | H | CO—O—CH₂—C≡CH | H | H | (±)-[1α,4aα,8aβ] | |
| 1.39 | SH | CO—O—CH₂—C₆H₅ | H | H | (±)-[1α,4aα,8aβ] | |
| 1.40 | H | CO—O—CH₂—C₆H₅ | H | H | (±)-[1α,4aα,8aβ] | |
| 1.41 | SH | CO—O—CH₂—OCH₃ | H | H | (±)-[1α,4aα,8aβ] | |
| 1.42 | H | CO—O—CH₂—OCH₃ | H | H | (±)-[1α,4aα,8aβ] | |
| 1.43 | SH | CO—NH—C₂H₅ | H | H | (±)-[1α,4aα,8aβ] | |
| 1.44 | H | CO—NH—C₂H₅ | H | H | (±)-[1α,4aα,8aβ] | |
| 1.45 | SH | CO—NH—C₃H₇—n | H | H | (±)-[1α,4aα,8aβ] | |
| 1.46 | H | CO—NH—C₃H₇—n | H | H | (±)-[1α,4aα,8aβ] | |
| 1.47 | SH | CO—NH—C₄H₉—n | H | H | (±)-[1α,4aα,8aβ] | |
| 1.48 | H | CO—NH—C₄H₉—n | H | H | (±)-[1α,4aα,8aβ] | |
| 1.49 | SH | CO—NH₂ | H | H | (±)-[1α,4aα,8aβ] | |
| 1.50 | H | CO—NH₂ | H | H | (±)-[1α,4aα,8aβ] | mp. 207.7° C. |
| 1.51 | SH | CO—NH—OCH₃ | H | H | (±)-[1α,4aα,8aβ] | |
| 1.52 | H | CO—NH—OCH₃ | H | H | (±)-[1α,4aα,8aβ] | |
| 1.53 | SH | CO—NH—C₃H₅—cycl. | H | H | (±)-[1α,4aα,8aβ] | |
| 1.54 | H | CO—NH—C₃H₅—cycl. | H | H | (±)-[1α,4aα,8aβ] | |
| 1.55 | SH | CO—SCH₃ | H | H | (±)-[1α,4aα,8aβ] | |
| 1.56 | H | CO—SCH₃ | H | H | (±)-[1α,4aα,8aβ] | |
| 1.57 | SH | CO—NH—NH₂ | H | H | (±)-[1α,4aα,8aβ] | |
| 1.58 | H | CO—NH—NH₂ | H | H | (±)-[1α,4aα,8aβ] | |
| 1.59 | SH | CO—NH—NH—CH₃ | H | H | (±)-[1α,4aα,8aβ] | |
| 1.60 | H | CO—NH—NH—CH₃ | H | H | (±)-[1α,4aα,8aβ] | |
| 1.61 | SH | CO—1-pyrrolidinyl | H | H | (±)-[1α,4aα,8aβ] | |
| 1.62 | H | CO—1-pyrrolidinyl | H | H | (±)-[1α,4aα,8aβ] | |
| 1.63 | H | CO—N(CH₃)₂ | H | H | (±)-[1α,4aα,8aβ] | mp. 111.5° C. |
| 1.64 | H | CO—NH—(CH₂)₂—OH | H | H | (±)-[1α,4aα,8aβ] | mp. 141.4° C. |
| 1.65 | H | CN | H | H | (±)-[1α,4aα,8aβ] | .HCl/mp. 203.4° C. |
| 1.66 | H | COOCH₃ | 2CH₃ | 2CH₃ | (±)-[1α,4aβ,8aβ] | HNO₃/mp. 151.7° C. |
| 1.67 | H | COOCH₃ | 2CH₃ | 2CH₃ | (±)-[1α,4aβ,8aβ] | |
| 1.68 | H | COOCH₃ | 2CH₃ | 2CH₃ | (±)-[1α,4aα,8aβ] | |
| 1.69 | H | COOCH₃ | 8a-CH₃ | H | | |
| 1.70 | H | COOCH₃ | 8a-CH₃ | H | | |

TABLE 2

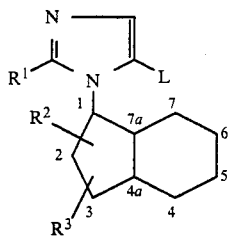

| Comp. No. | R¹ | R^{10-a} | R² | R³ | stereochemistry | physical data |
|---|---|---|---|---|---|---|
| 2.01 | SH | COOCH₃ | H | H | | mp. 144.9° C. |
| 2.02 | H | COOCH₃ | H | H | | (A + B + C)/HCl/mp. 146.6° C. |
| 2.03 | H | COOCH₃ | H | H | | (C)/HCl/mp. 153.5° C. |
| 2.04 | H | COOH | H | H | | (A + B + C)/mp. 213.2° C. |
| 2.05 | H | CONH—CH₃ | H | H | | (A + B + C)/HCl/mp. 221.4° C. |
| 2.06 | H | CN | H | H | | |
| 2.07 | SH | COOCH₃ | 2-CH₃ | 2-CH₃ | 4a,7a-cis | mp. 158-160° C. |
| 2.08 | H | COOCH₃ | 2-CH₃ | 2-CH₃ | 4a,7a-cis | mp. 62-64° C. |
| 2.09 | H | COOH | 2-CH₃ | 2-CH₃ | | |
| 2.10 | H | CONHCH₃ | 2-CH₃ | 2-CH₃ | | |
| 2.11 | H | CN | 2-CH₃ | 2-CH₃ | | |
| 2.12 | H | COOCH₃ | 2-CH₃ | 2-CH₃ | | |

TABLE 3

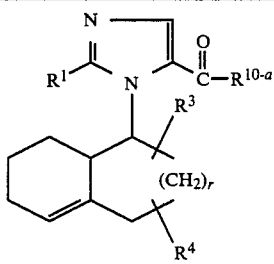

| Comp. No. | R¹ | R^{10-a} | r | R³ | R⁴ | physical data |
|---|---|---|---|---|---|---|
| 3.1 | SH | OCH₃ | 2 | 2-CH₃ | 2-CH₃ | |
| 3.2 | H | OCH₃ | 2 | 2-CH₃ | 2-CH₃ | |
| 3.3 | H | OH | 2 | 2-CH₃ | 2-CH₃ | |
| 3.4 | H | NH—CH₃ | 2 | 2-CH₃ | 2-CH₃ | |
| 3.5 | SH | OCH₃ | 2 | H | H | |
| 3.6 | H | OCH₃ | 2 | H | H | |
| 3.7 | SH | OCH₃ | 1 | 2-CH₃ | 2-CH₃ | |
| 3.8 | H | OCH₃ | 1 | 2-CH₃ | 2-CH₃ | |

TABLE 4

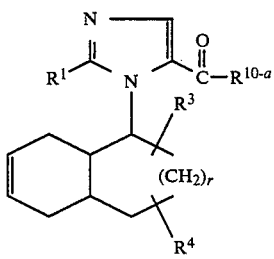

| Comp. No. | R¹ | R^{10-a} | r | R³ | R⁴ | physical data |
|---|---|---|---|---|---|---|
| 4.1 | SH | OCH₃ | 2 | H | H | |
| 4.2 | H | OCH₃ | 2 | H | H | |
| 4.3 | H | OH | 2 | H | H | |
| 4.4 | H | NH—CH₃ | 2 | H | H | |

TABLE 4-continued

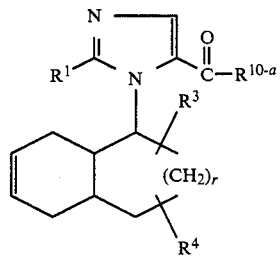

| Comp. No. | R¹ | R^{10-a} | r | R³ | R⁴ | physical data |
|---|---|---|---|---|---|---|
| 4.5 | SH | OCH₃ | 2 | 2-CH₃ | 2-CH₃ | |
| 4.6 | H | OCH₃ | 2 | 2-CH₃ | 2-CH₃ | |
| 4.7 | SH | OCH₃ | 1 | 2-CH₃ | 2-CH₃ | |
| 4.8 | H | OCH₃ | 1 | 2-CH₃ | 2-CH₃ | |

TABLE 5

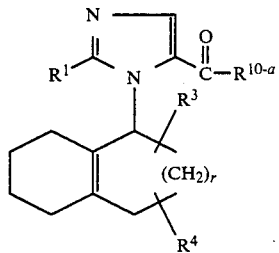

| Comp. No. | R¹ | R^{10-a} | r | R³ | R⁴ | physical data |
|---|---|---|---|---|---|---|
| 5.1 | SH | OCH₃ | 2 | 2-CH₃ | 2-CH₃ | |
| 5.2 | H | OCH₃ | 2 | 2-CH₃ | 2-CH₃ | |
| 5.3 | H | OH | 2 | 2-CH₃ | 2-CH₃ | |
| 5.4 | H | NH—CH₃ | 2 | 2-CH₃ | 2-CH₃ | |
| 5.5 | SH | OCH₃ | 2 | H | H | |
| 5.6 | H | OCH₃ | 2 | H | H | |
| 5.7 | SH | OCH₃ | 1 | 2-CH₃ | 2-CH₃ | |
| 5.8 | H | OCH₃ | 1 | 2-CH₃ | 2-CH₃ | |

TABLE 6

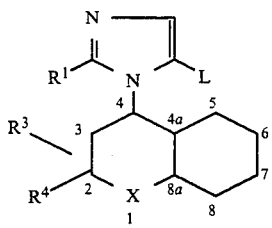

| Comp. No. | R¹ | L | X | R³ | R⁴ | physical data |
|---|---|---|---|---|---|---|
| 6.01 | SH | COOCH₃ | O | H | H | solid |
| 6.02 | H | COOCH₃ | O | H | H | (±)-[4α,8aα,4aβ].HNO₃/mp. 158.7° C. |
| 6.03 | H | COOCH₃ | O | H | H | (±)-[4β,8aα,4aβ] HNO₃/mp. 172.7° C. |
| 6.04 | H | COOH | O | H | H | |
| 6.05 | H | CO—NH—CH₃ | O | H | H | (A + B + C)/mp. 77.6° C. |
| 6.06 | SH | COOCH₃ | O | 2-CH₃ | 2-CH₃ | (±)-[4β,8aα,4aβ]/mp. 242.7° C. |
| 6.07 | H | COOCH₃ | O | H | H | (±)-[4β,8aα,4aβ]/.HNO₃/mp. 169.9° C. |
| 6.08 | H | COOCH₃ | O | 2-CH₃ | 2-CH₃ | 4a,8a-cis/.HNO₃/mp. 163.8° C. |
| 6.09 | H | COOH | O | H | H | |
| 6.10 | H | CO—NH—CH₃ | O | H | H | (±)-[4β,4aα,4aβ]/mp. 188.3° C. |
| 6.11 | H | COOCH₃ | S | H | H | |
| 6.12 | H | COOH | S | H | H | |
| 6.13 | H | CO—NH—CH₃ | S | H | H | |
| 6.14 | H | COOCH₃ | S | 2-CH₃ | 2-CH₃ | |
| 6.15 | H | COOH | S | 2-CH₃ | 2-CH₃ | |
| 6.16 | H | CO—NH—CH₃ | S | 2-CH₃ | 2-CH₃ | |
| 6.17 | H | COOCH₃ | SO | H | H | |
| 6.18 | H | COOCH₃ | SO₂ | H | H | |
| 6.20 | H | COOCH₃ | SO | 2-CH₃ | 2-CH₃ | |
| 6.21 | H | COOCH₃ | SO₂ | 2-CH₃ | 2-CH₃ | |
| 6.22 | SH | COOCH₃ | N—CH₃ | H | H | |
| 6.23 | H | COOCH₃ | N—CH₃ | H | H | |

TABLE 7

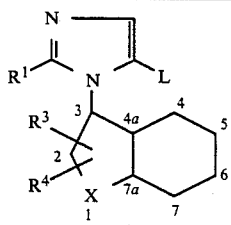

| Comp. No. | R¹ | L | X | R³ | R⁴ | physical data |
|---|---|---|---|---|---|---|
| 7.01 | SH | COOCH₃ | O | H | H | |
| 7.02 | H | COOCH₃ | O | H | H | |
| 7.03 | H | COOH | O | H | H | |
| 7.04 | H | CO—NH—CH₃ | O | H | H | |
| 7.05 | H | COOCH₃ | O | 2-CH₃ | 2-CH₃ | |
| 7.06 | H | COOH | O | 2-CH₃ | 2-CH₃ | |
| 7.07 | H | CO—NH—CH₃ | O | 2-CH₃ | 2-CH₃ | |
| 7.08 | H | COOCH₃ | S | H | H | |
| 7.09 | H | CO—NH—CH₃ | S | H | H | |
| 7.10 | H | COOCH₃ | S | 2-CH₃ | 2-CH₃ | |
| 7.11 | H | CO—NH—CH₃ | S | 2-CH₃ | 2-CH₃ | |
| 7.12 | H | COOCH₃ | SO | 2-CH₃ | 2-CH₃ | |
| 7.13 | H | COOCH₃ | SO₂ | 2-CH₃ | 2-CH₃ | |

TABLE 8

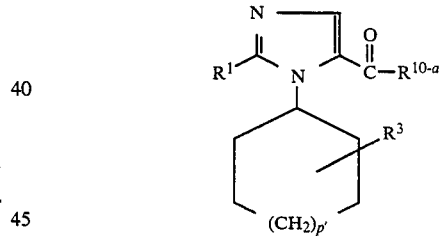

| Comp. No. | R¹ | R³ | R¹⁰⁻ᵃ | p' | physical data |
|---|---|---|---|---|---|
| 8.01 | SH | | OCH₃ | 2 | mp. 148.8° C. |
| 8.02 | H | | OCH₃ | 2 | .HNO₃/mp. 131.6° C. |
| 8.03 | H | | OH | 2 | mp. 207.1° C. |
| 8.04 | H | | NH—CH₃ | 2 | mp. 141.1° C. |
| 8.05 | SH | | OCH₃ | 3 | mp. 154.0° C. |
| 8.06 | H | | OCH₃ | 3 | .HNO₃/mp. 118.6° C. |
| 8.07 | H | | OH | 3 | mp. 217.2° C. |
| 8.08 | H | | NH—CH₃ | 3 | mp. 112.0° C. |
| 8.09 | SH | | OCH₃ | 5 | mp. 146.7° C. |
| 8.10 | H | | OCH₃ | 5 | .HNO₃/mp. 159.2° C. |
| 8.11 | H | | OH | 5 | mp. 208.5° C. |
| 8.12 | H | | NH—CH₃ | 5 | |
| 8.13 | SH | | OCH₃ | 7 | solid residue |
| 8.14 | H | | OCH₃ | 7 | .HNO₃/mp. 182.4° C. |
| 8.15 | H | | OH | 7 | mp. 209.0° C. |
| 8.16 | H | | NH—CH₃ | 7 | |
| 8.17 | SH | H | O—CH₃ | 0 | mp. 140° C. |
| 8.18 | H | H | O—CH₃ | 0 | oil |
| 8.19 | H | 2-phenyl | O—CH₃ | 1 | mp. 79–87° C. |
| 8.20 | H | 2-phenyl | OH | 1 | mp. 118° C.(dec.) |
| 8.21 | SH | 4-t. butyl | OCH₃ | 1 | mp. 173–174° C. |

TABLE 8-continued

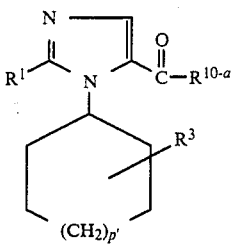

| Comp. No. | R¹ | R³ | R¹⁰⁻ᵃ | p' | physical data |
|---|---|---|---|---|---|
| 8.22 | H | 4-t. butyl | OCH₃ | 1 | mp. 87–101° C. |
| 8.23 | H | 4-t. butyl | OH | 1 | mp. 218° C.(dec.) |
| 8.24 | H | 4-t. butyl | NH₂ | 1 | mp. 177–191° C. |
| 8.25 | H | 4-t. butyl | NH—C₃H₇—n | 1 | mp. 154–166° C. |
| 8.26 | H | 4-t. butyl | NH—CH₃ | 1 | mp. 157–172° C. |
| 8.27 | H | 4-t. butyl | O—C₂H₅ | 1 | resin |

TABLE 9

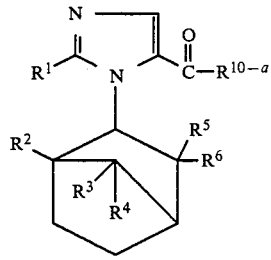

| Comp. No. | R¹ | R¹⁰⁻ᵃ | R² | R³ | R⁴ | R⁵ | R⁶ | physical data [α]$_D$ c = 1% in methanol |
|---|---|---|---|---|---|---|---|---|
| 9.01 | SH | OCH₃ | CH₃ | CH₃ | CH₃ | H | H | (±) mp. 161.2° C. |
| 9.02 | SH | OCH₃ | CH₃ | CH₃ | CH₃ | H | H | (1R, 2RS, 4R)/(+) [α]$_D$ = +17.4°/mp. 151.3° C. |
| 9.03 | SH | OCH₃ | CH₃ | CH₃ | CH₃ | H | H | (−) |
| 9.04 | H | OCH₃ | CH₃ | CH₃ | CH₃ | H | H | (±) HNO₃/mp. 173.5° C. |
| 9.05 | H | OCH₃ | CH₃ | CH₃ | CH₃ | H | H | (1R, 2RS, 4R)/(−)HNO₃/ [α]$_D$ = −21.30°/mp. 174.8° C. |
| 9.06 | H | OCH₃ | CH₃ | CH₃ | CH₃ | H | H | (+) |
| 9.07 | H | OH | CH₃ | CH₃ | CH₃ | H | H | (±) ½H₂O/mp. 201.6° C. |
| 9.08 | H | OH | CH₃ | CH₃ | CH₃ | H | H | (+) |
| 9.09 | H | OH | CH₃ | CH₃ | CH₃ | H | H | (−) [α]$_D$ = −31.85° mp. 232.6° C. |
| 9.10 | H | NH—CH₃ | CH₃ | CH₃ | CH₃ | H | H | (±) HNO₃/mp. 193.1° C. |
| 9.11 | H | NH—CH₃ | CH₃ | CH₃ | CH₃ | H | H | (+) |
| 9.12 | H | NH—CH₃ | CH₃ | CH₃ | CH₃ | H | H | (−) |
| 9.13 | SH | OCH₃ | H | H | H | H | H | (+) |
| 9.14 | H | OCH₃ | H | H | H | H | H | (+) |
| 9.15 | H | OH | H | H | H | H | H | (+) |
| 9.16 | H | NH—CH₃ | H | H | H | H | H | (+) |
| 9.17 | SH | OCH₃ | H | H | H | H | H | (−) |
| 9.18 | H | OCH₃ | H | H | H | H | H | (−) |
| 9.19 | H | OH | H | H | H | H | H | (−) |
| 9.20 | H | NH—CH₃ | H | H | H | H | H | (−) |
| 9.21 | SH | O—CH₃ | H | H | H | H | H | (endo + exo)/mp. 157.7° C. |
| 9.22 | H | O—CH₃ | H | H | H | H | H | (endo + exo)/HNO₃/mp. 182.1° C. |
| 9.23 | H | OH | H | H | H | H | H | (endo + exo)/mp. 259.9° C. |
| 9.24 | H | NH—CH₃ | H | H | H | H | H | (endo + exo)/mp. 145.4° C. |
| 9.25 | SH | O—CH₃ | H | H | H | H | H | (exo)/mp. 167° C. |
| 9.26 | H | O—CH₃ | H | H | H | H | H | (exo)/mp. 86° C. |
| 9.27 | H | OH | H | H | H | H | H | (exo)/mp. 231.1° C. |
| 9.28 | H | NH—CH₃ | H | H | H | H | H | (exo)/mp. 136° C. |
| 9.29 | SH | O—CH₃ | CH₃ | CH₃ | CH₃ | H | H | (1S, 2RS, 4S)/mp. 153.4° C. |
| 9.30 | H | O—CH₃ | CH₃ | CH₃ | CH₃ | H | H | (1S, 2RS, 4S)/.HNO₃/solid |
| 9.31 | H | OH | CH₃ | CH₃ | CH₃ | H | H | (1S, 2RS, 4S)/.HNO₃/solid |
| 9.32 | SH | OCH₃ | CH₃ | CH₃ | CH₃ | H | H | (1S, 2S, 4S)/solid residue |
| 9.33 | H | OCH₃ | CH₃ | CH₃ | CH₃ | H | H | (−)-(1S, 2S, 4S)/.HNO₃ mp. 200° C./[α]$_D$ = −1.59° |
| 9.34 | H | OH | CH₃ | CH₃ | CH₃ | H | H | (−)-(1S, 2S, 4S)/ mp. 233.8° C./[α]$_D$ = −4.33° |
| 9.35 | SH | OCH₃ | CH₃ | CH₃ | CH₃ | H | H | (−)-(1S, 2R, 4S)/ mp. 146.3° C./[α]$_D$ = −9.09° (0.1% in methanol) |
| 9.36 | H | OCH₃ | CH₃ | CH₃ | CH₃ | H | H | (1S, 2R, 4S)/.HNO₃ mp. 190° C. |
| 9.37 | H | OH | CH₃ | CH₃ | CH₃ | H | H | (+)-(1S, 2R, 4S)/ mp. 224.9° C./[α]$_D$ = +7.46° |
| 9.38 | SH | OCH₃ | CH₃ | CH₃ | CH₃ | H | H | (1R, 2S, 4R)/solid residue |
| 9.39 | H | OCH₃ | CH₃ | CH₃ | CH₃ | H | H | (1R, 2S, 4R)/mp. 112.8° C. |
| 9.40 | H | OH | CH₃ | CH₃ | CH₃ | H | H | (−)-(1R, 2S, 4R)/ mp. 225.1° C./[α]$_D$ = −151.23° |
| 9.41 | H | ON=(CH₃)₂ | CH₃ | CH₃ | CH₃ | H | H | mp. 119.9° C. |
| 9.42 | SH | OCH₃ | CH₃ | H | H | CH₃ | CH₃ | (1R, 2R, 4S)/solid |
| 9.43 | H | OCH₃ | CH₃ | H | H | CH₃ | CH₃ | (1R, 2R, 4S).HNO₃/ mp. 189.6° C. |
| 9.44 | H | OH | CH₃ | H | H | CH₃ | CH₃ | (1R, 2R, 4S)/mp. 215.3° C. |

TABLE 9-continued

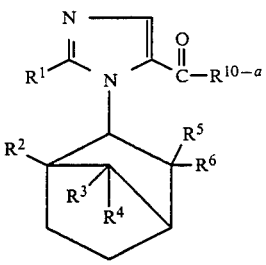

| Comp. No. | R¹ | R¹⁰⁻ᵃ | R² | R³ | R⁴ | R⁵ | R⁶ | physical data $[\alpha]_D$ c = 1% in methanol |
|---|---|---|---|---|---|---|---|---|
| 9.45 | H | NH—CH₃ | CH₃ | H | H | CH₃ | CH₃ | (1R, 2R, 4S) |
| 9.46 | SH | OCH₃ | CH₃ | H | H | CH₃ | CH₃ | (1R, 2RS, 4S) |
| 9.47 | SH | OCH₃ | CH₃ | H | H | CH₃ | CH₃ | (1R, 2S, 4S) |
| 9.48 | H | OCH₃ | CH₃ | H | H | CH₃ | CH₃ | (1R, 2RS, 4S) |
| 9.49 | H | OCH₃ | CH₃ | H | H | CH₃ | CH₃ | (1R, 2S, 4S) |
| 9.50 | H | OH | CH₃ | H | H | CH₃ | CH₃ | (1R, 2RS, 4S) |
| 9.51 | H | OH | CH₃ | H | H | CH₃ | CH₃ | (1R, 2S, 4S) |
| 9.52 | H | NH—CH₃ | CH₃ | H | H | CH₃ | CH₃ | (1R, 2RS, 4S) |
| 9.53 | H | NH—CH₃ | CH₃ | H | H | CH₃ | CH₃ | (1R, 2S, 4S) |

TABLE 10

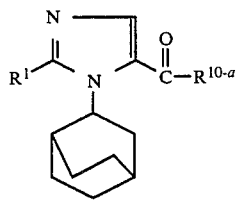

| Comp. no. | R¹ | R¹⁰⁻ᵃ | physical data |
|---|---|---|---|
| 10.01 | SH | OCH₃ | |
| 10.02 | H | OCH₃ | |
| 10.03 | H | OCH₃ | |
| 10.04 | H | NH—CH₃ | |

TABLE 12

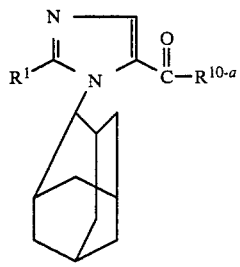

| Comp. no. | R¹ | R¹⁰⁻ᵃ | physical data |
|---|---|---|---|
| 12.01 | SH | OCH₃ | mp. 198.0° C. |
| 12.02 | H | OCH₃ | |
| 12.03 | H | OCH₃ | .HNO₃/mp. 196.9° C. |

TABLE 11

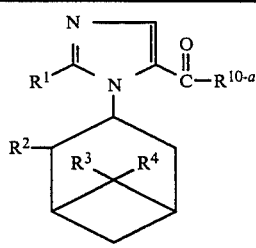

| Comp. No. | R¹ | R¹⁰⁻ᵃ | R² | R³ | R⁴ | physical data $[\alpha]_D$ c = 1% in methanol |
|---|---|---|---|---|---|---|
| 11.01 | SH | OCH₃ | CH₃ | CH₃ | CH₃ | (±) mp. 177.8° C. |
| 11.02 | SH | OCH₃ | CH₃ | CH₃ | CH₃ | (+) |
| 11.03 | SH | OCH₃ | CH₃ | CH₃ | CH₃ | (−) |
| 11.04 | H | OCH₃ | CH₃ | CH₃ | CH₃ | (±) .HNO₃/mp. 164.4° C. |
| 11.05 | H | OCH₃ | CH₃ | CH₃ | CH₃ | (+) |
| 11.06 | H | OCH₃ | CH₃ | CH₃ | CH₃ | (−) |
| 11.07 | H | OH | CH₃ | CH₃ | CH₃ | (±) mp. 195.7° C. |
| 11.08 | H | OH | CH₃ | CH₃ | CH₃ | (+) |
| 11.09 | H | OH | CH₃ | CH₃ | CH₃ | (−) |
| 11.10 | H | NH—CH₃ | CH₃ | CH₃ | CH₃ | (±) mp. 161.9° C. |
| 11.11 | H | NH—CH₃ | CH₃ | CH₃ | CH₃ | (+) |
| 11.12 | H | NH—CH₃ | CH₃ | CH₃ | CH₃ | (−) |
| 11.13 | SH | OCH₃ | H | H | H | |
| 11.14 | H | OCH₃ | H | H | H | |
| 11.15 | H | OH | H | H | H | |
| 11.16 | H | NH—CH₃ | H | H | H | |

TABLE 12-continued

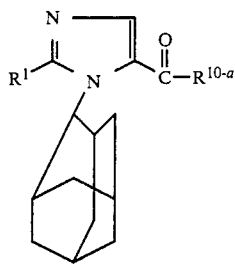

| Comp. no. | R¹ | R¹⁰⁻ᵃ | physical data |
|---|---|---|---|
| 12.04 | H | OH | mp. 247.0° C. |
| 12.05 | H | NH—CH₃ | |

TABLE 13

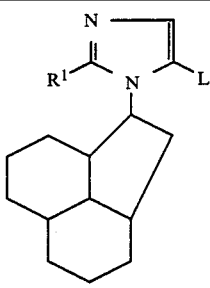

| Comp. no. | R¹ | L | physical data |
|---|---|---|---|
| 13.01 | SH | COOCH₃ | mp. 179° C. |
| 13.02 | H | COOCH₃ | |
| 13.03 | H | COOH | |
| 13.04 | H | CONHCH₃ | |

C. Composition Examples

EXAMPLE 16

Composition examples for solid compounds of formula (I) (percentages are by weight)

| (a) Wettable powders | (a) | (b) | (c) |
|---|---|---|---|
| compound of formula (I) | 20% | 50% | 0.5% |
| sodium lignosulfonate | 5% | 5% | 5% |
| sodium laurylsulfate | 3% | — | — |
| sodium diisobutylnaphthalenesulfonate | — | 6% | 6% |
| octylphenol polyethylene glycol ether (7–8 moles of ethylene oxide) | — | 2% | 2% |
| highly dispersed silicic acid | 5% | 27% | 27% |
| kaolin | 67% | 10% | — |
| sodium chloride | — | — | 59.5% |

The active ingredient was thoroughly mixed with the adjuvants and the mixture was thoroughly ground in a suitable mill, affording wettable powders which could be diluted with water to give suspensions of the desired concentration.

| (b) Emulsifiable concentrate | (a) | (b) |
|---|---|---|
| compound of formula (I) | 10% | 1% |
| octylphenol polyethylene glycol ether (4–5 moles of ethylene oxide) | 3% | 3% |
| calcium dodecylbenzenesulfonate | 3% | 3% |
| castor oil polyglycol ether (36 moles of ethylene oxide) | 4% | 4% |
| cyclohexanone | 30% | 10% |
| dimethylbenzene mixture | 50% | 79% |

Emulsions of any required concentration could be obtained from this concentrate by dilution with water.

| (c) Dusts | (a) | (b) |
|---|---|---|
| compound of formula (I) | 0.1% | 1% |
| talcum | 99.9% | — |
| kaolin | — | 99% |

Usable dusts were obtained by mixing the active ingredient with the carriers, and grinding the mixture in a suitable mill.

| (d) Extruder granulate | (a) | (b) |
|---|---|---|
| compound of formula (I) | 10% | 1% |
| sodium lignosulfate | 2% | 2% |
| carboxymethylcellulose | 1% | 1% |
| kaolin | 87% | 96% |

The active ingredient was mixed and ground with the adjuvants, and the mixture was subsequently moistened with water. The mixture was extruded and dried in a stream of air.

| (e) Coated granulate | |
|---|---|
| compound of formula (I) | 3% |
| polyethylene glycol (mol. wt. 200) | 2% |
| kaolin | 95% |

The finely ground active ingredient was uniformly applied, in a mixer, to the kaolin moistened with polyethylene glycol. Non-dusty coated granulates were obtained in this manner.

| (f) Suspension concentrate | (a) | (b) |
|---|---|---|
| compound of formula (I) | 40% | 5% |
| ethylene glycol | 10% | 10% |
| nonylphenol polyethylene glycol ether (15 moles of ethylene oxide) | 6% | 1% |
| sodium lignosulfate | 10% | 5% |
| carboxymethylcellulose | 1% | 1% |
| 37% aqueous formaldehyde solution | 0.2% | 0.2% |
| silicone oil in the form of a 75% aqueous emulsion | 0.8% | 0.8% |
| water | 32% | 77% |

The finely ground active ingredient was intimately mixed with the adjuvants, giving a suspension concentrate from which suspension of any desired concentration could be obtained by dilution with water.

| (g) Salt solution | |
|---|---|
| compound of formula (I) | 5% |
| isopropylamine | 1% |
| octylphenol polyethylene glycol ether (78 moles of ethylene oxide) | 3% |
| water | 91% |

EXAMPLE 17

Composition examples for liquid active ingredients of formula (I) (throughout, percentages are by weight)

| (a) Emulsifiable concentrates | (a) | (b) | (c) |
|---|---|---|---|
| compound of formula (I) | 20% | 40% | 50% |
| calcium dodecylbenzenesulfonate | 5% | 8% | 5.8% |
| castor oil polyethylene glycol ether (36 moles of ethylene oxide) | 5% | — | — |
| tributylphenol polyethylene glycol ether (30 moles of ethylene oxide) | — | 12% | 4.2% |
| cyclohexanone | — | 15% | 20% |
| dimethylbenzene mixture | 70% | 25% | 20% |

Emulsions of any required concentration could be produced from such concentrate by dilution with water.

| (b) Solutions | (a) | (b) | (c) | (d) |
|---|---|---|---|---|
| compound of formula (I) | 80% | 10% | 5% | 95% |
| ethylene glycol monoethyl ether | 20% | — | — | — |
| polyethylene glycol (MG 400) | — | 70% | — | — |
| N—methyl-2-pyrrolidone | — | 20% | — | — |
| epoxidised coconut oil | — | — | 1% | 5% |
| petroleum distillate (boiling range 160–190° C.) | — | — | 94% | — |

These solutions were suitable for application in the form of microdrops.

| (c) Granulates | (a) | (b) |
|---|---|---|
| compound of formula (I) | 5% | 10% |
| kaolin | 94% | — |
| highly dispersed silicic acid | 1% | — |
| attapulgite | — | 90% |

The active ingredient was dissolved in methylene chloride, the solution was sprayed onto the carrier, and the solvent was subsequently evaporated off in vacuo.

| (d) Dusts | (a) | (b) |
|---|---|---|
| compound of formula (I) | 2% | 5% |
| highly dispersed silicic acid | 1% | 5% |
| talcum | 97% | — |
| kaolin | — | 90% |

D. Biological examples

EXAMPLE 18

Preemergence herbicidal action

In a greenhouse, immediately after sowing the test plants in seed dishes, the surface of the soil was treated with an aqueous dispersion of the test compounds, obtained from a 25% emulsifiable concentrate or from a 25% wettable powder with test compounds, which, on account of their insufficient solubility, could not be formulated to emulsifiable concentrates. Two different concentration series were used, corresponding to 1 to 0.5 kg of test compound per hectare respectively. The seed dishes were kept in the greenhouse at 22°~25° C. and 50~70% relative humidity. The test was evaluated 3 weeks later in accordance with the following rating:
1 = plants had not germinated or were totally withered
2–3 = very stong action
4–6 = avery action
7–8 = slight action
9 = no action Results: Preemergence test dosage: 4 kg active ingredient per hectare

| plant tested compound tested | digitaria | poa | bro-mus | setaria | echinochloa | maize |
|---|---|---|---|---|---|---|
| 1.12 | 3 | 5 | 1 | 5 | 3 | 9 |
| 1.64 | 1 | 1 | 2 | 1 | 1 | 8 |
| 2.02 | 2 | 1 | 5 | 5 | 1 | 9 |
| 6.05 | 1 | 1 | 3 | 1 | 1 | 7 |
| 10.08 | 1 | 1 | 3 | 1 | 1 | 9 |

| plant tested compound tested | digitaria | poa | bro-mus | setaria | echinochloa | rice |
|---|---|---|---|---|---|---|
| 1.50 | 1 | 1 | 1 | 1 | 1 | 7 |
| 1.63 | 1 | 1 | 9 | 1 | 6 | 8 |
| 1.66 | 3 | 1 | 9 | 3 | 1 | 8 |
| 6.03 | 1 | 3 | 7 | 4 | 3 | 7 |
| 8.19 | 1 | 1 | 3 | 1 | 1 | 7 |
| 9.04 | 1 | 3 | 7 | 4 | 3 | 8 |
| 9.05 | 3 | 5 | 9 | 1 | 3 | 9 |

EXAMPLE 19

Postemergence herbicidal action (Contact herbicide)

A large number of weeds and cultivated plants were sprayed postemergence in the 4- to 6-leaf stage with an aqueous active ingredient dispersion in rates of 4 and 2 kg of test compound per hectare and kept at 24°~26° C. and 45~60% relative humidity. The test was evaluated at least 15 days after treatment in accordance with the same rating as employed in the preemergence test.

Results: dosage 4 kg active ingredient per hectare

| plant tested compound tested | solanum | sinapis | phaseolus |
|---|---|---|---|
| 1.05 | 2 | 2 | 2 |
| 1.08 | 2 | 2 | 2 |
| 1.17 | 1 | 2 | 2 |
| 2.01 | 3 | 3 | 2 |
| 2.08 | 2 | 1 | 2 |
| 8.06 | 2 | 1 | 2 |
| 8.08 | 2 | 2 | 3 |
| 8.19 | 2 | 2 | 3 |
| 9.05 | 3 | 2 | 2 |
| 9.22 | 1 | 2 | 3 |
| 9.24 | 1 | 1 | 4 |
| 9.26 | 2 | 1 | 2 |

EXAMPLE 20

Herbicidal action against paddy rice associated weeds

The seeds of the waterweeds Echinochloa crus galli and Monochoria vaginalis were sown in plastic containers (60 cm² surface, 500 ml by volume) together. The containers were watered up to the soil surface and after three days the water level was raised slightly above the soil surface (3–5 mm). Three days after sowing an aqueous emulsion of the active compound was applied by spraying the containers at a rate of application of 4 kg of a.i. per hectare (dilution 550 l/ha). The containers were kept in a greenhouse for three weeks under conditions optimal for the waterweeds, i.e. at a temperature between 20° and 25° C. and under high humidity. The evaluation of the tests was made in accordance with the rating given in example 18.

| Results: dosage 4 kg active ingredient per hectare | | |
|---|---|---|
| plant tested compound tested | Echinochloa | Monochoria |
| 1.04 | 3 | 1 |
| 1.05 | 1 | 1 |
| 1.08 | 1 | 1 |
| 1.10 | 1 | 1 |
| 1.12 | 1 | 1 |
| 1.16 | 1 | 1 |
| 1.17 | 2 | 1 |
| 2.01 | 1 | 1 |
| 2.07 | 3 | 1 |
| 2.08 | 1 | 1 |
| 8.08 | 2 | 2 |
| 8.19 | 1 | 1 |
| 9.04 | 1 | 1 |
| 9.05 | 1 | 1 |
| 9.10 | 1 | 1 |
| 9.22 | 1 | 1 |
| 9.26 | 1 | 1 |

We claim:
1. A chemical compound having the formula

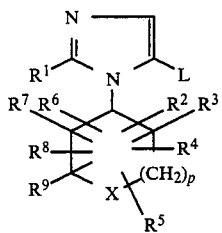 (I)

or a stereoisomeric form thereof, or a salt thereof, wherein
$R^1$ is hydrogen or mercapto;
L is cyano, $COOR^{10}$,

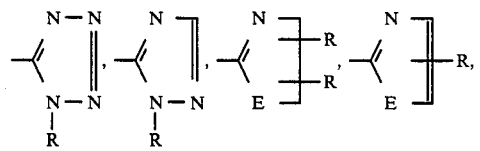

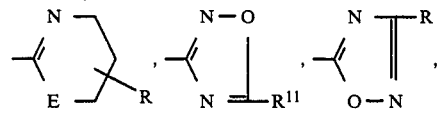

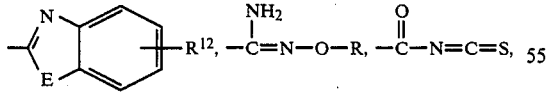

or a group of $-C(=G)-D-R^{13}$;
p is zero or the integer one to seven;
X is $CH_2$, O, S(O) or $NR^{14}$, wherein n is 0, 1 or 2;
$R^2$, $R^3$, $R^4$, $R^5$, $R^6$, $R^7$, $R^8$ and $R^9$ are each independently hydrogen, $C_1-C_6$alkyl, mono- and di(aryl)-$C_1-C_5$alkyl, hydroxy$C_1-C_5$alkyl, $C_1-C_5$alkyloxy$C_1-C_5$alkyl, $C_1-C_6$alkyloxy, halo, $C_3-C_7$alkenyl, trifluoromethyl, difluoromethoxy, or aryl; and two or four of the substituents $R^2$, $R^3$, $R^4$, $R^5$, $R^6$, $R^7$, $R^8$ or $R^9$ taken together form one or two bivalent $C_1-C_5$alkanediyl, or $C_3-C_5$alkenedi7yl or $C_5-C_7$-cycloalkanediyl radicals, said $C_1-C_5$alkanediyl, $C_3-C_5$alkenediyl or $C_5-7$ cycloalkanediyl which is unsubstituted or substituted where possible with up to four radicals selected from the group consisting of $C_1-C_5$alkyl, mono- and di(aryl)$C_1-C_5$alkyl, hydroxy$C_1-C_5$alkyl, $C_1-C_5$alkyloxy$C_1-C_5$alkyl, $C_1-C_6$alkyloxy, halo, $C_3-C_7$alkenyl, trifluromethyl, difluoromethoxy and aryl; or two or four of the substituents $R^2$, $R^3$, $R^4$, $R^5$, $R^6$, $R^7$, $R^8$ or $R^9$ being vicinally substituted may form one or two further bonds; and wherein one of the substituents on the said bivalent $C_1-C_5$alkanediyl, $C_3-C_5$alkenediyl or $C_5-C_7$cycloalkandiyl taken together with one of the substituents $R^2$, $R^3$, $R^4$, $R^5$, $R^6$, $R^7$, $R^8$ and $R^9$ may also form a bivalent $C_1-C_5$alkanediyl or $C_3-C_5$alkenediyl bridge which in turn may be substituted where possible with up to four radicals selected from the group consisting of $C_1-C_6$alkyl, mono- and di(aryl)$C_1-C_5$alkyl, hydroxy$C_1-C_5$alkyl, $C_1-C_5$alkyloxy$C_1-C_5$alkyl, $C_1-C_6$alkyloxy, halo, $C_3-C_7$alkenyl, trifluoromethyl, difluoromethoxy and aryl;
$R^{10}$ is hydrogen, $C_1-C_7$alkyl which is unsubstituted or substituted with one, two or three halo atoms, $C_3-C_7$alkenyl, $C_3-C_7$alkynyl, $C_3-C_7$cycloalkyl, $C_1-C_7$alkyloxy$C_1-C_7$alkyl, aryl$C_1-C_5$alkyl or a radical of formula $-N=C(R^{15})_2$;
E ix oxygen, sulfur or $-NR-$;
R is hydrogen or $C_1-C_5$alkyl;
$R^{11}$ is hydrogen, $C_1-C_5$alkyl or trifluoromethyl;
$R^{12}$ is hydrogen, $C_1-C_5$alkyl, $C_1-C_5$alkyloxy, halo, trifluoromethyl, difluoromethoxy, cyano, nitro, amino, mono- and $diC^1-C^5$alkylamino or $C^1-C^5$alkylcarbonylamino;
$R^{15}$ is hydrogen, $C_1-C_5$alkyl or two $R^{15}$ radicals may form a $C_4-C_6$alkanediyl radical;
G is $=N-R^{16}$, oxygen or sulfur;
D is sulfur, $-N(R^{17})-$, $-N(R^{18})-NH-$, $-N(R^{18})-O-$, $$-\underset{|}{N}-C(=G)-OR^{18}, -\underset{|}{N}-C(=G)-R^{18}, -\underset{|}{N}SO_2-R^{18},$$

$-\underset{|}{N}-CN$, $-NH-CH_2-CH_2-O-$ or $$-N-CH_2-CH_2-O-;\\ |\\ CH_2-CH_2-OH$$

$R^{13}$, $R^{17}$ and $R^{18}$ are independently selected from hydrogen, $C_1-C_5$alkyl, $C_3-C_5$alkenyl, C;hd 3-$C_5$alkynyl, $C_3-C_7$cycloalkyl or $C_1-C_5$alkyl substituted with aryl, $C_3-C_7$cycloalkyl, $C_3-C_7$cycloalkyloxy, $C_1-C_5$alkyloxy, hydroxy, carboxyl or $C_1-C_5$alkyloxycarbonyl, whereas $R^{18}$ may also be aryl; or
$R^{13}$ and $R^{17}$ together with the nitrogen atom to which they are attached may form a piperidinyl, pyrrolidinyl, 2-oxopiperidinyl, 2-oxopyrrolidinyl, morpholinyl, thiomorpholinyl, piperazinyl or 4-($C_1-C_5$alkyl)piperazinyl ring, each unsubstituted or substituted with one to three $C_1-C_5$alkyl groups;

$R^{14}$ is hydrogen, $C_1$–$C_5$alkyl, $C_1$–$C_5$alkanoyl, or 4-methylphenylsulfonyl; and $R^{16}$ is hydrogen or $C_1$–$C_5$alkyl;

aryl is phenyl which is unsubstituted or substituted with one to three substitutents each independently selected from $C_1$–$C_5$alkyl, $C_1$–$C_5$alkyloxy and halo.

2. A chemical compound according to claim 1 wherein the 1-substituent of the 1H-imidazole ring is a radical of formula

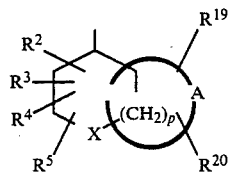

(a)

wherein A is $C_1$–$C_5$alkanediyl or $C_3$–$C_5$alkenediyl; X and $R^2$, $R^3$, $R^4$ and $R^5$ are as defined hereinabove and $R^{19}$ and $R^{20}$ independently have the same meaning of said $R^2$, $R^3$, $R^4$ and $R^5$.

3. A chemical compound according to claim 1 wherein the 1-substituent of the 1H-imidazole ring is a radical of formula

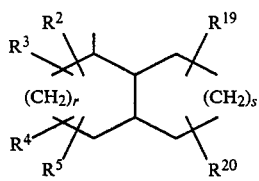

(b)

wherein r and s independently are one, two or three; and in the $(CH_2)_s$-containing ring one or two pairs of vicinal hydrogen atoms may be abstracted to form one or two extra bonds.

4. A compound according to claim 2 wherein L is $COOR^{10}$, CN or a radical —C(=O)—D—$R^{13}$.

5. A compound according to claim 4 wherein $R^{10}$ is hydrogen or $C_1$–$C_7$alkyl, G is O, D is $NR^{17}$, and $R^{13}$ and $R^{17}$ are hydrogen or $C_1$–$C_5$alkyl.

6. A compound according to claim 1 wherein the compound is methyl 1-(decahydro-1-naphthalenyl)-1H-imidazole-5-carboxylate.

7. A herbicidal composition comprising an inert carrier and, if desired, other adjuvants and as active ingredient a herbicidally effective amount of chemical compound having the formula (I) as claimed in claim 1.

8. A composition according to claim 7 wherein the 1-substituent of the 1H-imidazole ring is a radical of formula

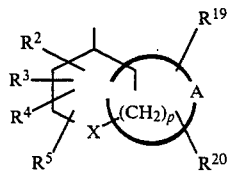

(a)

wherein A is $C_1$–$C_5$alkanediyl or $C_3$–$C_5$alkenediyl; X and $R^2$, $R^3$, $R^4$ and $R^5$ are as defined hereinabove and $R^{19}$ and $R^{20}$ independently have the same meaning of said $R^2$, $R^3$, $R^4$ and $R^5$.

9. A composition according to claim 7 wherein the 1-substituent of the 1H-imidazole ring is a radical of formula

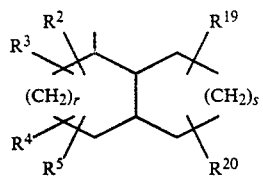

(b)

wherein r and s independently are one, two or three; and in the $(CH_2)_s$-containing ring one or two pairs of vicinal hydrogen atoms may be abstracted to form one or two extra bonds.

10. A composition according to claim 9 wherein L is $COOR^{10}$, CN or a radical —C(=O)—D—$R^{13}$.

11. A composition according to claim 10 wherein $R^{10}$ is hydrogen or $C_1$–$C_7$alkyl, G is O, D is $NR^{17}$, and $R^{13}$ and $R^{17}$ are hydrogen or $C_1$–$C_5$alkyl.

12. A composition according to claim 7 wherein the compound is methyl 1-(decahydro-1-naphthalenyl)-1H-imidazole-5-carboxylate.

13. A method for controlling weeds comprising the application to said weeds or to the locus thereof of a herbicidally effective amount of a compound of formula (I) as claimed in claim 1.

14. A method according to claim 13 for selectively controlling weeds in crops of useful plants.

15. A method according to claim 14 wherein the crop is rice, maize or cereals.

16. A method according to claim 14 wherein the crop is rice and the rice is transplanted rice.

17. A method according to claim 15, wherein 0.01 to 5 kg of active ingredient per hectare are applied to areas where rice crops are grown.

18. A method according to claim 17 wherein 0.05 to 1 kg of the active ingredient is applied per hectare after transplanting the rice plantlets.

19. A method according to claim 13 wherein the 1-substituent of the 1H-imidazole ring is a radical of formula

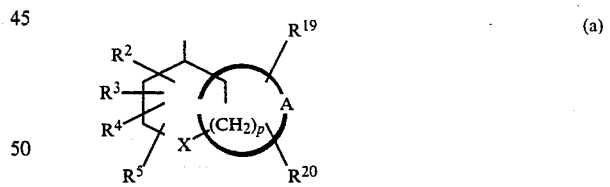

(a)

wherein A is $C_1$–$C_5$alkanediyl or $C_3$–$C_5$alkenediyl; X and $R^2$, $R^3$, $R^4$ and $R^5$ are as defined hereinabove and $R^{19}$ and $R^{20}$ independently have the same meaning of said $R^2$, $R^3$, $R^4$ and $R^5$.

20. A method according to claim 13 wherein the 1-substituent of the 1H-imidazole ring is a radical of formula

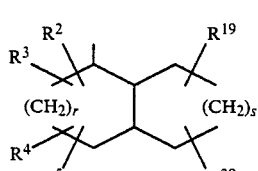

(b)

wherein r and s independently are one, two or three; and in the $(CH_2)_s$- containing ring one or two pairs of vicinal hydrogen atoms may be abstracted to form one or two extra bonds.

21. A method according to claim 19 wherein L is $COOR^{10}$, CN or a radical —C(=O)—D—$R^{13}$.

22. A method according to claim 21 wherein $R^{10}$ is hydrogen or $C_1$–$C_7$alkyl, G is O, D is $NR^{17}$, and $R^{13}$ and $R^{17}$ are hydrogen or $C_1$–$C_5$alkyl.

23. A method according to claim 13 wherein the compound is methyl 1-(decahydro-1-naphthalenyl)-1$\underline{H}$-imidazole-5-carboxylate.

* * * * *